United States Patent
Hawkins et al.

(10) Patent No.: US 9,839,530 B2
(45) Date of Patent: Dec. 12, 2017

(54) HIGHLY LORDOSED FUSION CAGE

(71) Applicant: DePuy Synthes Products, Inc., Raynham, MA (US)

(72) Inventors: John Riley Hawkins, Cumberland, RI (US); Anwar Upal, Fall River, MA (US); Michael J. O'Neil, West Barnstable, MA (US); Michael Andrew Slivka, Berkley, MA (US); Michael Fisher, Lawrenceville, GA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 15/193,305

(22) Filed: Jun. 27, 2016

(65) Prior Publication Data

US 2016/0302938 A1    Oct. 20, 2016

Related U.S. Application Data

(60) Continuation of application No. 14/514,700, filed on Oct. 15, 2014, now Pat. No. 9,402,737, which is a
(Continued)

(51) Int. Cl.
*A61F 2/44* (2006.01)
*A61F 2/46* (2006.01)
*A61F 2/30* (2006.01)

(52) U.S. Cl.
CPC .......... *A61F 2/447* (2013.01); *A61F 2/30771* (2013.01); *A61F 2/442* (2013.01); *A61F 2/4455* (2013.01); *A61F 2/4611* (2013.01); *A61F 2/30744* (2013.01); *A61F 2/30965* (2013.01); *A61F 2002/3008* (2013.01); *A61F 2002/3038* (2013.01); *A61F 2002/30062* (2013.01); *A61F 2002/3093* (2013.01); *A61F 2002/30331* (2013.01); *A61F 2002/30387* (2013.01); *A61F 2002/30403* (2013.01); (Continued)

(58) Field of Classification Search
CPC .......... A61F 2/44; A61F 2/4455; A61F 2/447
USPC .......................................... 623/17.11–17.16
See application file for complete search history.

(56) References Cited

U.S. PATENT DOCUMENTS

| | | |
|---|---|---|
| 1,802,560 A | 4/1931 | Kerwin et al. |
| 2,077,804 A | 4/1937 | Monroe et al. |

(Continued)

FOREIGN PATENT DOCUMENTS

| | | |
|---|---|---|
| AU | 2005314079 | 10/2012 |
| CN | 1177918 | 4/1998 |

(Continued)

OTHER PUBLICATIONS

U.S. Appl. No. 61/675,975, filed Jul. 26, 2012, Lechmann et al.
(Continued)

*Primary Examiner* — Matthew Lawson
(74) *Attorney, Agent, or Firm* — Baker & Hostetler LLP

(57) ABSTRACT

A fusion cage has a first component that defines an outside surface that is configured to engage a vertebral endplate, and an interior surface. The fusion cage has a second component that defines first and second opposed surfaces. One of the first and second opposed surfaces can mate with the interior surface of the first component. The fusion cage can include vertical and lateral throughholes adapted to enhance fusion.

23 Claims, 11 Drawing Sheets

Related U.S. Application Data division of application No. 11/768,636, filed on Jun. 26, 2007, now Pat. No. 8,900,307.

(52) U.S. Cl.
CPC .............. *A61F 2002/30438* (2013.01); *A61F 2002/30448* (2013.01); *A61F 2002/30457* (2013.01); *A61F 2002/30481* (2013.01); *A61F 2002/30579* (2013.01); *A61F 2002/30604* (2013.01); *A61F 2002/30685* (2013.01); *A61F 2002/30841* (2013.01); *A61F 2002/30904* (2013.01); *A61F 2002/30975* (2013.01); *A61F 2002/448* (2013.01); *A61F 2002/4475* (2013.01); *A61F 2002/4627* (2013.01); *A61F 2002/4629* (2013.01); *A61F 2210/0004* (2013.01); *A61F 2220/0016* (2013.01); *A61F 2220/0025* (2013.01); *A61F 2220/0033* (2013.01); *A61F 2250/0098* (2013.01); *A61F 2310/00017* (2013.01); *A61F 2310/00023* (2013.01); *A61F 2310/00029* (2013.01); *A61F 2310/00059* (2013.01); *A61F 2310/00161* (2013.01); *A61F 2310/00203* (2013.01); *A61F 2310/00239* (2013.01)

(56) References Cited

U.S. PATENT DOCUMENTS

| | | |
|---|---|---|
| 2,121,193 A | 6/1938 | Hanicke |
| 2,173,655 A | 9/1939 | Neracher et al. |
| 2,243,717 A | 5/1941 | Godoy et al. |
| 2,381,050 A | 8/1945 | Hardinge et al. |
| 2,388,056 A | 10/1945 | Hendricks et al. |
| 2,485,531 A | 10/1949 | William et al. |
| 2,489,870 A | 11/1949 | William et al. |
| 2,570,465 A | 10/1951 | Lundholm et al. |
| 2,677,369 A | 5/1954 | Knowles et al. |
| 3,115,804 A | 12/1963 | Lee et al. |
| 3,312,139 A | 4/1967 | Di et al. |
| 3,486,505 A | 12/1969 | Morrison et al. |
| 3,489,143 A | 1/1970 | Halloran et al. |
| 3,698,391 A | 10/1972 | Mahony et al. |
| 3,760,802 A | 9/1973 | Fischer et al. |
| 3,805,775 A | 4/1974 | Fischer et al. |
| 3,811,449 A | 5/1974 | Gravlee et al. |
| 3,842,825 A | 10/1974 | Wagner |
| 3,848,601 A | 11/1974 | Ma et al. |
| 3,867,728 A | 2/1975 | Stubstad et al. |
| 3,986,504 A | 10/1976 | Avila |
| 4,013,071 A | 3/1977 | Rosenberg |
| 4,052,988 A | 10/1977 | Doddi et al. |
| 4,091,806 A | 5/1978 | Aginsky |
| 4,175,555 A | 11/1979 | Herbert |
| 4,236,512 A | 12/1980 | Aginsky |
| 4,262,665 A | 4/1981 | Roalstad et al. |
| 4,275,717 A | 6/1981 | Bolesky |
| 4,312,353 A | 1/1982 | Shahbabian |
| 4,341,206 A | 7/1982 | Perrett et al. |
| 4,349,921 A | 9/1982 | Kuntz |
| 4,350,151 A | 9/1982 | Scott |
| 4,369,790 A | 1/1983 | McCarthy |
| 4,401,112 A | 8/1983 | Rezaian |
| 4,401,433 A | 8/1983 | Luther |
| 4,409,974 A | 10/1983 | Freedland |
| 4,449,532 A | 5/1984 | Storz |
| 4,451,256 A | 5/1984 | Weikl et al. |
| 4,456,005 A | 6/1984 | Lichty |
| 4,463,753 A | 8/1984 | Gustilo |
| 4,488,543 A | 12/1984 | Tornier |
| 4,494,535 A | 1/1985 | Haig |
| 4,532,660 A | 8/1985 | Field |
| 4,537,185 A | 8/1985 | Stednitz |
| 4,545,374 A | 10/1985 | Jacobson |
| 4,573,448 A | 3/1986 | Kambin |
| 4,601,710 A | 7/1986 | Moll |
| 4,625,725 A | 12/1986 | Davison et al. |
| 4,629,450 A | 12/1986 | Suzuki et al. |
| 4,632,101 A | 12/1986 | Freedland |
| 4,640,271 A | 2/1987 | Lower |
| 4,641,640 A | 2/1987 | Griggs |
| 4,653,489 A | 3/1987 | Tronzo |
| 4,667,663 A | 5/1987 | Miyata |
| 4,686,984 A | 8/1987 | Bonnet |
| 4,688,561 A | 8/1987 | Reese |
| 4,721,103 A | 1/1988 | Freedland |
| 4,723,544 A | 2/1988 | Moore et al. |
| 4,743,256 A | 5/1988 | Brantigan |
| 4,743,257 A | 5/1988 | Tormala et al. |
| 4,759,766 A | 7/1988 | Buettner-Janz et al. |
| 4,760,843 A | 8/1988 | Fischer et al. |
| 4,790,304 A | 12/1988 | Rosenberg |
| 4,790,817 A | 12/1988 | Luther |
| 4,796,612 A | 1/1989 | Reese |
| 4,802,479 A | 2/1989 | Haber et al. |
| 4,815,909 A | 3/1989 | Simons |
| 4,827,917 A | 5/1989 | Brumfield |
| 4,858,601 A | 8/1989 | Glisson |
| 4,862,891 A | 9/1989 | Smith |
| 4,863,476 A | 9/1989 | Shepperd |
| 4,871,366 A | 10/1989 | von Recum et al. |
| 4,873,976 A | 10/1989 | Schreiber |
| 4,878,915 A | 11/1989 | Brantigan |
| 4,898,186 A | 2/1990 | Ikada et al. |
| 4,903,692 A | 2/1990 | Reese |
| 4,917,554 A | 4/1990 | Bronn |
| 4,940,467 A | 7/1990 | Tronzo |
| 4,959,064 A | 9/1990 | Engelhardt |
| 4,963,144 A | 10/1990 | Huene |
| 4,966,587 A | 10/1990 | Baumgart |
| 4,968,317 A | 11/1990 | Tormala et al. |
| 4,978,334 A | 12/1990 | Toye et al. |
| 4,978,349 A | 12/1990 | Frigg |
| 4,981,482 A | 1/1991 | Ichikawa |
| 4,988,351 A | 1/1991 | Paulos et al. |
| 4,994,027 A | 2/1991 | Farrell |
| 5,002,557 A | 3/1991 | Hasson |
| 5,011,484 A | 4/1991 | Breard |
| 5,013,315 A | 5/1991 | Barrows |
| 5,013,316 A | 5/1991 | Goble et al. |
| 5,059,193 A | 10/1991 | Kuslich |
| 5,062,849 A | 11/1991 | Schelhas |
| 5,071,437 A | 12/1991 | Steffee |
| 5,080,662 A | 1/1992 | Paul |
| 5,084,043 A | 1/1992 | Hertzmann et al. |
| 5,092,891 A | 3/1992 | Kummer et al. |
| 5,098,241 A | 3/1992 | Aldridge et al. |
| 5,098,433 A | 3/1992 | Freedland |
| 5,098,435 A | 3/1992 | Stednitz et al. |
| 5,114,407 A | 5/1992 | Burbank |
| 5,116,336 A | 5/1992 | Frigg |
| 5,120,171 A | 6/1992 | Lasner |
| 5,122,133 A | 6/1992 | Evans |
| 5,122,141 A | 6/1992 | Simpson et al. |
| 5,123,926 A | 6/1992 | Pisharodi |
| 5,139,486 A | 8/1992 | Moss |
| 5,158,543 A | 10/1992 | Lazarus |
| 5,167,663 A | 12/1992 | Brumfield |
| 5,167,664 A | 12/1992 | Hodorek |
| 5,169,400 A | 12/1992 | Muhling et al. |
| 5,171,278 A | 12/1992 | Pisharodi |
| 5,171,279 A | 12/1992 | Mathews |
| 5,171,280 A | 12/1992 | Baumgartner |
| 5,176,651 A | 1/1993 | Allgood et al. |
| 5,176,697 A | 1/1993 | Hasson et al. |
| 5,178,501 A | 1/1993 | Carstairs |
| 5,183,464 A | 2/1993 | Dubrul et al. |
| 5,188,118 A | 2/1993 | Terwilliger |
| 5,195,506 A | 3/1993 | Hulfish |
| 5,201,742 A | 4/1993 | Hasson |
| 5,217,462 A | 6/1993 | Asnis et al. |
| 5,217,486 A | 6/1993 | Rice et al. |
| 5,224,952 A | 7/1993 | Deniega et al. |

(56) References Cited

U.S. PATENT DOCUMENTS

| | | |
|---|---|---|
| 5,234,431 A | 8/1993 | Keller |
| 5,241,972 A | 9/1993 | Bonati |
| 5,242,410 A | 9/1993 | Melker |
| 5,242,447 A | 9/1993 | Borzone |
| 5,246,441 A | 9/1993 | Ross et al. |
| 5,250,049 A | 10/1993 | Michael |
| 5,269,797 A | 12/1993 | Bonati et al. |
| 5,280,782 A | 1/1994 | Wilk |
| 5,286,001 A | 2/1994 | Rafeld |
| 5,290,243 A | 3/1994 | Chodorow et al. |
| 5,290,312 A | 3/1994 | Kojimoto et al. |
| 5,300,074 A | 4/1994 | Frigg |
| 5,304,142 A | 4/1994 | Liebl et al. |
| 5,308,327 A | 5/1994 | Heaven et al. |
| 5,308,352 A | 5/1994 | Koutrouvelis |
| 5,312,410 A | 5/1994 | Miller et al. |
| 5,312,417 A | 5/1994 | Wilk |
| 5,314,477 A | 5/1994 | Marnay |
| 5,324,261 A | 6/1994 | Amundson et al. |
| 5,334,184 A | 8/1994 | Bimman |
| 5,334,204 A | 8/1994 | Clewett et al. |
| 5,342,365 A | 8/1994 | Waldman |
| 5,342,382 A | 8/1994 | Brinkerhoff et al. |
| 5,344,252 A | 9/1994 | Kakimoto |
| 5,364,398 A | 11/1994 | Chapman et al. |
| 5,370,646 A | 12/1994 | Reese et al. |
| 5,370,647 A | 12/1994 | Graber et al. |
| 5,370,661 A | 12/1994 | Branch |
| 5,370,697 A | 12/1994 | Baumgartner |
| 5,382,248 A | 1/1995 | Jacobson et al. |
| 5,387,213 A | 2/1995 | Breard et al. |
| 5,387,215 A | 2/1995 | Fisher |
| 5,390,683 A | 2/1995 | Pishardi |
| 5,395,317 A | 3/1995 | Kambin |
| 5,395,371 A | 3/1995 | Miller et al. |
| 5,401,269 A | 3/1995 | Buttner-Janz et al. |
| 5,407,430 A | 4/1995 | Peters |
| 5,415,661 A | 5/1995 | Holmes |
| 5,424,773 A | 6/1995 | Saito |
| 5,425,773 A | 6/1995 | Boyd et al. |
| 5,443,514 A | 8/1995 | Steffee |
| 5,449,359 A | 9/1995 | Groiso |
| 5,449,361 A | 9/1995 | Preissman |
| 5,452,748 A | 9/1995 | Simmons et al. |
| 5,454,790 A | 10/1995 | Dubrul |
| 5,464,427 A | 11/1995 | Curtis et al. |
| 5,470,333 A | 11/1995 | Ray |
| 5,472,426 A | 12/1995 | Bonati et al. |
| 5,474,539 A | 12/1995 | Costa et al. |
| 5,486,190 A | 1/1996 | Green |
| 5,496,318 A | 3/1996 | Howland et al. |
| 5,498,265 A | 3/1996 | Asnis et al. |
| 5,501,695 A | 3/1996 | Anspach, Jr. et al. |
| 5,505,710 A | 4/1996 | Dorsey, III |
| 5,507,816 A | 4/1996 | Bullivant |
| 5,512,037 A | 4/1996 | Russell et al. |
| 5,514,180 A | 5/1996 | Heggeness et al. |
| 5,520,690 A | 5/1996 | Errico et al. |
| 5,520,896 A | 5/1996 | de Graaf et al. |
| 5,522,899 A | 6/1996 | Michelson |
| 5,527,312 A | 6/1996 | Ray |
| 5,534,029 A | 7/1996 | Shima |
| 5,536,127 A | 7/1996 | Pennig |
| 5,540,688 A | 7/1996 | Navas |
| 5,540,693 A | 7/1996 | Fisher |
| 5,545,164 A | 8/1996 | Howland |
| 5,549,610 A | 8/1996 | Russell et al. |
| 5,554,191 A | 9/1996 | Lahille et al. |
| 5,556,431 A | 9/1996 | Buttner-Janz |
| 5,558,674 A | 9/1996 | Heggeness et al. |
| D374,287 S | 10/1996 | Goble et al. |
| 5,562,738 A | 10/1996 | Boyd et al. |
| 5,564,926 A | 10/1996 | Brånemark |
| 5,569,248 A | 10/1996 | Mathews |
| 5,569,251 A | 10/1996 | Baker et al. |
| 5,569,290 A | 10/1996 | McAfee |
| 5,569,548 A | 10/1996 | Koike et al. |
| 5,591,168 A | 1/1997 | Judet et al. |
| 5,609,634 A | 3/1997 | Voydeville |
| 5,609,635 A | 3/1997 | Michelson |
| 5,613,950 A | 3/1997 | Yoon |
| 5,618,142 A | 4/1997 | Sonden et al. |
| 5,618,314 A | 4/1997 | Harwin et al. |
| 5,624,447 A | 4/1997 | Myers |
| 5,626,613 A | 5/1997 | Schmieding |
| 5,628,751 A | 5/1997 | Sander et al. |
| 5,628,752 A | 5/1997 | Asnis et al. |
| 5,639,276 A | 6/1997 | Weinstock et al. |
| 5,643,320 A | 7/1997 | Lower et al. |
| 5,645,589 A | 7/1997 | Li |
| 5,645,599 A | 7/1997 | Samani |
| 5,647,857 A | 7/1997 | Anderson et al. |
| 5,649,931 A | 7/1997 | Bryant et al. |
| 5,653,763 A | 8/1997 | Errico |
| 5,658,335 A | 8/1997 | Allen |
| 5,662,683 A | 9/1997 | Kay |
| 5,665,095 A | 9/1997 | Jacobson |
| 5,665,122 A | 9/1997 | Kambin |
| 5,667,508 A | 9/1997 | Errico et al. |
| 5,669,915 A | 9/1997 | Caspar et al. |
| 5,676,701 A | 10/1997 | Yuan et al. |
| 5,683,465 A | 11/1997 | Shinn et al. |
| 5,693,100 A | 12/1997 | Pisharodi |
| 5,697,977 A | 12/1997 | Pisharodi |
| 5,702,391 A | 12/1997 | Lin |
| 5,707,359 A | 1/1998 | Bufalini |
| 5,713,870 A | 2/1998 | Yoon |
| 5,713,903 A | 2/1998 | Sander et al. |
| 5,716,415 A | 2/1998 | Steffee |
| 5,716,416 A | 2/1998 | Lin |
| 5,720,753 A | 2/1998 | Sander et al. |
| 5,725,541 A | 3/1998 | Anspach, III et al. |
| 5,725,588 A | 3/1998 | Errico et al. |
| 5,728,097 A | 3/1998 | Mathews |
| 5,728,116 A | 3/1998 | Rosenman |
| 5,735,853 A | 4/1998 | Olerud |
| 5,741,282 A | 4/1998 | Anspach, III et al. |
| 5,743,881 A | 4/1998 | Demco |
| 5,743,912 A | 4/1998 | Lahille et al. |
| 5,743,914 A | 4/1998 | Skiba |
| 5,749,889 A | 5/1998 | Bacich et al. |
| 5,752,969 A | 5/1998 | Cunci et al. |
| 5,762,500 A | 6/1998 | Lazarof |
| 5,762,629 A | 6/1998 | Kambin |
| 5,772,661 A | 6/1998 | Michelson |
| 5,772,662 A | 6/1998 | Chapman et al. |
| 5,772,678 A | 6/1998 | Thomason et al. |
| 5,776,156 A | 7/1998 | Shikhman |
| 5,782,800 A | 7/1998 | Yoon |
| 5,782,832 A | 7/1998 | Larsen et al. |
| 5,782,865 A | 7/1998 | Grotz |
| 5,792,044 A | 8/1998 | Foley et al. |
| 5,797,909 A | 8/1998 | Michelson |
| 5,810,721 A | 9/1998 | Mueller et al. |
| 5,810,821 A | 9/1998 | Vandewalle |
| 5,810,866 A | 9/1998 | Yoon |
| 5,814,084 A | 9/1998 | Grivas et al. |
| 5,836,948 A | 11/1998 | Zucherman et al. |
| 5,846,259 A | 12/1998 | Berthiaume |
| 5,849,004 A | 12/1998 | Bramlet |
| 5,851,216 A | 12/1998 | Allen |
| 5,860,973 A | 1/1999 | Michelson |
| 5,860,977 A | 1/1999 | Zucherman et al. |
| 5,865,848 A | 2/1999 | Baker |
| 5,871,485 A | 2/1999 | Rao et al. |
| 5,873,854 A | 2/1999 | Wolvek |
| 5,876,404 A | 3/1999 | Zucherman et al. |
| 5,888,224 A | 3/1999 | Beckers et al. |
| 5,888,226 A | 3/1999 | Rogozinski |
| 5,888,227 A | 3/1999 | Cottle |
| 5,888,228 A | 3/1999 | Knothe et al. |
| 5,893,850 A | 4/1999 | Cachia |
| 5,893,889 A | 4/1999 | Harrington |
| 5,893,890 A | 4/1999 | Pisharodi |

(56) References Cited

U.S. PATENT DOCUMENTS

| | | |
|---|---|---|
| 5,895,428 A | 4/1999 | Berry |
| 5,902,231 A | 5/1999 | Foley et al. |
| 5,904,696 A | 5/1999 | Rosenman |
| 5,908,422 A | 6/1999 | Bresina |
| 5,928,235 A | 7/1999 | Friedl |
| 5,928,244 A | 7/1999 | Tovey et al. |
| 5,931,870 A | 8/1999 | Cuckler et al. |
| 5,935,129 A | 8/1999 | McDevitt et al. |
| 5,947,999 A | 9/1999 | Groiso |
| 5,948,000 A | 9/1999 | Larsen et al. |
| 5,954,722 A | 9/1999 | Bono |
| 5,954,747 A | 9/1999 | Clark |
| 5,957,902 A | 9/1999 | Teves |
| 5,964,730 A | 10/1999 | Williams et al. |
| 5,964,761 A | 10/1999 | Kambin |
| 5,967,783 A | 10/1999 | Ura |
| 5,967,970 A | 10/1999 | Cowan et al. |
| 5,968,044 A | 10/1999 | Nicholson et al. |
| 5,968,098 A | 10/1999 | Winslow |
| 5,976,139 A | 11/1999 | Bramlet |
| 5,976,146 A | 11/1999 | Ogawa et al. |
| 5,976,186 A | 11/1999 | Bao et al. |
| 5,980,522 A * | 11/1999 | Koros ............... A61F 2/4455 606/60 |
| 5,984,927 A | 11/1999 | Wenstrom, Jr. et al. |
| 5,984,966 A | 11/1999 | Kiema et al. |
| 5,989,255 A | 11/1999 | Pepper et al. |
| 5,989,291 A | 11/1999 | Ralph et al. |
| 5,993,459 A | 11/1999 | Larsen et al. |
| 5,997,510 A | 12/1999 | Schwemberger |
| 5,997,538 A | 12/1999 | Asnis et al. |
| 5,997,541 A | 12/1999 | Schenk |
| 6,001,100 A | 12/1999 | Sherman et al. |
| 6,001,101 A | 12/1999 | Augagneur et al. |
| 6,004,327 A | 12/1999 | Asnis et al. |
| 6,005,161 A | 12/1999 | Brekke et al. |
| 6,007,519 A | 12/1999 | Rosselli |
| 6,007,566 A | 12/1999 | Wenstrom, Jr. |
| 6,007,580 A | 12/1999 | Lehto et al. |
| 6,010,513 A | 1/2000 | Tormala et al. |
| 6,019,762 A | 2/2000 | Cole |
| 6,022,352 A | 2/2000 | Vandewalle |
| 6,030,162 A | 2/2000 | Huebner |
| 6,030,364 A | 2/2000 | Durgin et al. |
| 6,033,406 A | 3/2000 | Mathews |
| 6,036,701 A | 3/2000 | Rosenman |
| 6,039,761 A | 3/2000 | Li |
| 6,039,763 A | 3/2000 | Shelokov |
| 6,045,579 A | 4/2000 | Hochshuler |
| 6,048,309 A | 4/2000 | Flom et al. |
| 6,048,342 A | 4/2000 | Zucherman et al. |
| 6,053,935 A | 4/2000 | Brenneman et al. |
| 6,066,142 A | 5/2000 | Serbousek et al. |
| 6,068,630 A | 5/2000 | Zucherman et al. |
| 6,068,648 A | 5/2000 | Cole et al. |
| 6,074,390 A | 6/2000 | Zucherman et al. |
| 6,080,155 A | 6/2000 | Michelson |
| 6,080,193 A | 6/2000 | Hochshuler et al. |
| 6,083,244 A | 7/2000 | Lubbers et al. |
| 6,090,112 A | 7/2000 | Zucherman et al. |
| 6,096,038 A | 8/2000 | Michelson |
| 6,099,531 A | 8/2000 | Bonutti |
| 6,102,914 A | 8/2000 | Bulstra et al. |
| 6,102,950 A | 8/2000 | Vaccaro |
| 6,106,557 A | 8/2000 | Robioneck et al. |
| 6,113,637 A | 9/2000 | Gill et al. |
| 6,113,638 A | 9/2000 | Williams et al. |
| 6,117,174 A | 9/2000 | Nolan |
| 6,123,711 A | 9/2000 | Winters |
| 6,126,661 A | 10/2000 | Faccioli et al. |
| 6,126,663 A | 10/2000 | Hair |
| 6,127,597 A | 10/2000 | Beyar et al. |
| 6,129,762 A | 10/2000 | Li |
| 6,129,763 A | 10/2000 | Chauvin et al. |
| 6,146,384 A | 11/2000 | Lee et al. |
| 6,146,387 A | 11/2000 | Trott et al. |
| 6,149,652 A | 11/2000 | Zucherman et al. |
| 6,152,926 A | 11/2000 | Zucherman et al. |
| 6,156,038 A | 12/2000 | Zucherman et al. |
| 6,159,179 A | 12/2000 | Simonson |
| 6,161,350 A | 12/2000 | Espinosa |
| 6,162,234 A | 12/2000 | Freedland et al. |
| 6,162,236 A | 12/2000 | Osada |
| 6,168,595 B1 | 1/2001 | Durham et al. |
| 6,168,597 B1 | 1/2001 | Biedermann et al. |
| 6,175,758 B1 | 1/2001 | Kambin |
| 6,176,882 B1 | 1/2001 | Biedermann et al. |
| 6,179,794 B1 | 1/2001 | Burras |
| 6,179,873 B1 | 1/2001 | Zientek |
| 6,183,471 B1 | 2/2001 | Zucherman et al. |
| 6,183,472 B1 | 2/2001 | Lutz |
| 6,183,474 B1 | 2/2001 | Bramlet et al. |
| 6,183,517 B1 | 2/2001 | Suddaby |
| 6,190,387 B1 | 2/2001 | Zucherman et al. |
| 6,193,757 B1 | 2/2001 | Foley et al. |
| 6,197,041 B1 | 3/2001 | Shichman et al. |
| 6,200,322 B1 | 3/2001 | Branch et al. |
| 6,206,826 B1 | 3/2001 | Mathews et al. |
| 6,206,922 B1 | 3/2001 | Zdeblick et al. |
| 6,213,957 B1 | 4/2001 | Milliman et al. |
| 6,217,509 B1 | 4/2001 | Foley et al. |
| 6,221,082 B1 | 4/2001 | Marino et al. |
| 6,228,058 B1 | 5/2001 | Dennis et al. |
| 6,231,606 B1 | 5/2001 | Graf et al. |
| 6,235,030 B1 | 5/2001 | Zucherman et al. |
| 6,238,397 B1 | 5/2001 | Zucherman et al. |
| 6,245,107 B1 | 6/2001 | Ferree |
| 6,248,108 B1 | 6/2001 | Tormala et al. |
| 6,251,111 B1 | 6/2001 | Barker et al. |
| 6,264,676 B1 | 7/2001 | Gellman et al. |
| 6,267,765 B1 | 7/2001 | Taylor et al. |
| 6,267,767 B1 | 7/2001 | Strobel et al. |
| 6,280,444 B1 | 8/2001 | Zucherman et al. |
| 6,287,313 B1 | 9/2001 | Sasso |
| 6,293,909 B1 | 9/2001 | Chu et al. |
| 6,293,952 B1 | 9/2001 | Brosens et al. |
| 6,296,647 B1 | 10/2001 | Robioneck et al. |
| 6,302,914 B1 | 10/2001 | Michelson |
| 6,306,136 B1 | 10/2001 | Baccelli |
| 6,319,254 B1 | 11/2001 | Giet et al. |
| 6,319,272 B1 | 11/2001 | Brenneman et al. |
| 6,332,882 B1 | 12/2001 | Zucherman et al. |
| 6,332,883 B1 | 12/2001 | Zucherman et al. |
| 6,332,895 B1 | 12/2001 | Suddaby |
| 6,346,092 B1 | 2/2002 | Leschinsky |
| 6,348,053 B1 | 2/2002 | Cachia |
| 6,355,043 B1 | 3/2002 | Adam |
| 6,361,537 B1 | 3/2002 | Anderson |
| 6,361,538 B1 | 3/2002 | Fenaroli et al. |
| 6,361,557 B1 | 3/2002 | Gittings et al. |
| 6,364,897 B1 | 4/2002 | Bonutti |
| 6,368,350 B1 | 4/2002 | Erickson et al. |
| 6,368,351 B1 | 4/2002 | Glenn |
| 6,371,971 B1 | 4/2002 | Tsugita et al. |
| 6,371,989 B1 | 4/2002 | Chauvin et al. |
| 6,375,682 B1 | 4/2002 | Fleischmann et al. |
| 6,379,355 B1 | 4/2002 | Zucherman et al. |
| 6,379,363 B1 | 4/2002 | Herrington et al. |
| 6,387,130 B1 | 5/2002 | Stone |
| 6,409,766 B1 | 6/2002 | Brett |
| 6,419,676 B1 | 7/2002 | Zucherman et al. |
| 6,419,677 B2 | 7/2002 | Zucherman et al. |
| 6,419,704 B1 | 7/2002 | Ferree |
| 6,419,705 B1 | 7/2002 | Erickson |
| 6,419,706 B1 | 7/2002 | Graf |
| 6,423,061 B1 | 7/2002 | Bryant |
| 6,423,067 B1 | 7/2002 | Eisermann |
| 6,425,919 B1 | 7/2002 | Lambrecht |
| 6,428,541 B1 | 8/2002 | Boyd et al. |
| 6,428,556 B1 | 8/2002 | Chin |
| 6,436,140 B1 | 8/2002 | Liu et al. |
| 6,436,143 B1 | 8/2002 | Ross et al. |
| 6,440,154 B2 | 8/2002 | Gellman et al. |
| 6,440,169 B1 | 8/2002 | Elberg et al. |

(56) References Cited

U.S. PATENT DOCUMENTS

| | | |
|---|---|---|
| 6,443,989 B1 | 9/2002 | Jackson |
| 6,447,527 B1 | 9/2002 | Thompson et al. |
| 6,447,540 B1 | 9/2002 | Fontaine et al. |
| 6,450,989 B2 | 9/2002 | Dubrul et al. |
| 6,451,019 B1 | 9/2002 | Zucherman et al. |
| 6,451,020 B1 | 9/2002 | Zucherman et al. |
| 6,454,806 B1 | 9/2002 | Cohen et al. |
| 6,454,807 B1 | 9/2002 | Jackson |
| 6,458,134 B1 | 10/2002 | Songer et al. |
| 6,468,277 B1 | 10/2002 | Justin et al. |
| 6,468,309 B1 | 10/2002 | Lieberman |
| 6,468,310 B1 | 10/2002 | Ralph et al. |
| 6,471,724 B2 | 10/2002 | Zdeblick et al. |
| 6,475,226 B1 | 11/2002 | Belef et al. |
| 6,478,029 B1 | 11/2002 | Boyd et al. |
| 6,478,796 B2 | 11/2002 | Zucherman et al. |
| 6,485,491 B1 | 11/2002 | Farris et al. |
| 6,485,518 B1 | 11/2002 | Cornwall et al. |
| 6,488,693 B2 | 12/2002 | Gannoe et al. |
| 6,488,710 B2 | 12/2002 | Besselink |
| 6,489,309 B1 | 12/2002 | Singh et al. |
| 6,491,714 B1 | 12/2002 | Bennett |
| 6,494,860 B2 | 12/2002 | Rocamora et al. |
| 6,494,893 B2 | 12/2002 | Dubrul et al. |
| 6,500,178 B2 | 12/2002 | Zucherman et al. |
| 6,506,192 B1 | 1/2003 | Gertzman et al. |
| 6,511,481 B2 | 1/2003 | von Hoffmann et al. |
| 6,514,256 B2 | 2/2003 | Zucherman et al. |
| 6,517,543 B1 | 2/2003 | Berrevoets et al. |
| 6,517,580 B1 | 2/2003 | Ramadan et al. |
| 6,520,907 B1 | 2/2003 | Foley et al. |
| 6,527,774 B2 | 3/2003 | Lieberman |
| 6,527,803 B1 | 3/2003 | Crozet |
| 6,527,804 B1 | 3/2003 | Gauchet et al. |
| 6,533,818 B1 | 3/2003 | Weber et al. |
| 6,540,747 B1 | 4/2003 | Marino |
| 6,544,265 B2 | 4/2003 | Lieberman |
| 6,547,793 B1 | 4/2003 | McGuire |
| 6,547,795 B2 | 4/2003 | Schneiderman |
| 6,551,319 B2 | 4/2003 | Lieberman |
| 6,551,322 B1 | 4/2003 | Lieberman |
| 6,554,831 B1 | 4/2003 | Rivard et al. |
| 6,554,852 B1 | 4/2003 | Oberlander |
| 6,558,389 B2 | 5/2003 | Clark et al. |
| 6,558,424 B2 | 5/2003 | Thalgott |
| 6,562,046 B2 | 5/2003 | Sasso |
| 6,562,049 B1 | 5/2003 | Norlander et al. |
| 6,562,074 B2 | 5/2003 | Gerbec et al. |
| 6,575,979 B1 | 6/2003 | Cragg |
| 6,576,016 B1 | 6/2003 | Hochshuler et al. |
| 6,579,293 B1 | 6/2003 | Chandran |
| 6,582,390 B1 | 6/2003 | Sanderson |
| 6,582,431 B1 | 6/2003 | Ray |
| 6,582,433 B2 | 6/2003 | Yun |
| 6,582,437 B2 | 6/2003 | Dorchak et al. |
| 6,582,441 B1 | 6/2003 | He et al. |
| 6,582,453 B1 | 6/2003 | Tran et al. |
| 6,582,468 B1 | 6/2003 | Gauchet |
| 6,585,730 B1 | 7/2003 | Foerster |
| 6,585,740 B2 | 7/2003 | Schlapfer et al. |
| 6,589,240 B2 | 7/2003 | Hinchliffe |
| 6,589,249 B2 | 7/2003 | Sater et al. |
| 6,592,553 B2 | 7/2003 | Zhang et al. |
| 6,595,998 B2 | 7/2003 | Johnson et al. |
| 6,596,008 B1 | 7/2003 | Kambin |
| 6,599,297 B1 | 7/2003 | Carlsson et al. |
| 6,607,530 B1 | 8/2003 | Carl et al. |
| 6,610,091 B1 | 8/2003 | Reiley |
| 6,610,094 B2 | 8/2003 | Husson |
| 6,613,050 B1 | 9/2003 | Wagner et al. |
| 6,616,678 B2 | 9/2003 | Nishtala et al. |
| 6,620,196 B1 | 9/2003 | Trieu |
| 6,626,944 B1 | 9/2003 | Taylor |
| 6,632,224 B2 | 10/2003 | Cachia et al. |
| 6,635,059 B2 | 10/2003 | Randall et al. |
| 6,635,362 B2 | 10/2003 | Zheng |
| 6,641,564 B1 | 11/2003 | Kraus |
| 6,641,614 B1 | 11/2003 | Wagner et al. |
| 6,648,890 B2 | 11/2003 | Culbert et al. |
| 6,648,893 B2 | 11/2003 | Dudasik |
| 6,648,917 B2 | 11/2003 | Gerbec et al. |
| 6,652,527 B2 | 11/2003 | Zucherman et al. |
| 6,655,962 B1 | 12/2003 | Kennard |
| 6,666,891 B2 | 12/2003 | Boehm, Jr. et al. |
| 6,669,698 B1 | 12/2003 | Tromanhauser et al. |
| 6,669,729 B2 | 12/2003 | Chin |
| 6,669,732 B2 | 12/2003 | Serhan et al. |
| 6,673,074 B2 | 1/2004 | Shluzas |
| 6,676,664 B1 | 1/2004 | Al-Assir |
| 6,676,665 B2 | 1/2004 | Foley et al. |
| 6,679,833 B2 | 1/2004 | Smith et al. |
| 6,682,535 B2 | 1/2004 | Hoogland |
| 6,685,706 B2 | 2/2004 | Padget et al. |
| 6,685,742 B1 | 2/2004 | Jackson |
| 6,689,152 B2 | 2/2004 | Balceta et al. |
| 6,692,499 B2 | 2/2004 | Tormala et al. |
| 6,695,842 B2 | 2/2004 | Zucherman et al. |
| 6,695,851 B2 | 2/2004 | Zdeblick et al. |
| 6,699,246 B2 | 3/2004 | Zucherman et al. |
| 6,699,247 B2 | 3/2004 | Zucherman et al. |
| 6,706,070 B1 | 3/2004 | Wagner et al. |
| 6,712,819 B2 | 3/2004 | Zucherman et al. |
| 6,716,247 B2 | 4/2004 | Michelson |
| 6,719,760 B2 | 4/2004 | Dorchak et al. |
| 6,719,796 B2 | 4/2004 | Cohen et al. |
| 6,723,096 B1 | 4/2004 | Dorchak et al. |
| 6,723,126 B1 | 4/2004 | Berry |
| 6,730,126 B2 | 5/2004 | Boehm, Jr. et al. |
| 6,733,093 B2 | 5/2004 | Deland et al. |
| 6,733,460 B2 | 5/2004 | Ogura |
| 6,733,532 B1 | 5/2004 | Gauchet et al. |
| 6,733,534 B2 | 5/2004 | Sherman |
| 6,733,535 B2 | 5/2004 | Michelson |
| 6,733,635 B1 | 5/2004 | Ozawa et al. |
| 6,740,090 B1 | 5/2004 | Cragg et al. |
| 6,740,093 B2 | 5/2004 | Hochschuler et al. |
| 6,740,117 B2 | 5/2004 | Ralph et al. |
| 6,743,166 B2 | 6/2004 | Berci et al. |
| 6,743,255 B2 | 6/2004 | Ferree |
| 6,746,451 B2 | 6/2004 | Middleton et al. |
| 6,752,831 B2 | 6/2004 | Sybert et al. |
| 6,761,720 B1 | 7/2004 | Senegas |
| 6,770,075 B2 | 8/2004 | Howland |
| 6,790,210 B1 | 9/2004 | Cragg et al. |
| 6,793,656 B1 | 9/2004 | Mathews |
| 6,793,678 B2 | 9/2004 | Hawkins |
| 6,796,983 B1 | 9/2004 | Zucherman et al. |
| 6,805,685 B2 | 10/2004 | Taylor |
| 6,805,695 B2 | 10/2004 | Keith et al. |
| 6,805,714 B2 | 10/2004 | Sutcliffe |
| 6,808,526 B1 | 10/2004 | Magerl et al. |
| 6,808,537 B2 | 10/2004 | Michelson |
| 6,821,298 B1 | 11/2004 | Jackson |
| 6,824,565 B2 | 11/2004 | Muhanna |
| 6,830,589 B2 | 12/2004 | Erickson |
| 6,835,205 B2 | 12/2004 | Atkinson et al. |
| 6,835,206 B2 | 12/2004 | Jackson |
| 6,855,167 B2 | 2/2005 | Shimp |
| 6,863,673 B2 | 3/2005 | Gerbec et al. |
| 6,875,215 B2 | 4/2005 | Taras et al. |
| 6,881,229 B2 | 4/2005 | Khandkar et al. |
| 6,887,243 B2 | 5/2005 | Culbert |
| 6,890,333 B2 | 5/2005 | von Hoffmann et al. |
| 6,893,464 B2 | 5/2005 | Kiester |
| 6,893,466 B2 | 5/2005 | Trieu |
| 6,902,566 B2 | 6/2005 | Zucherman et al. |
| 6,908,465 B2 | 6/2005 | von Hoffmann et al. |
| 6,916,323 B2 | 7/2005 | Kitchens |
| 6,921,403 B2 | 7/2005 | Cragg et al. |
| 6,923,811 B1 | 8/2005 | Carl et al. |
| 6,929,606 B2 | 8/2005 | Ritland |
| 6,936,071 B1 | 8/2005 | Marnay et al. |
| 6,936,072 B2 | 8/2005 | Lambrecht et al. |
| 6,942,668 B2 | 9/2005 | Padget et al. |

(56) References Cited

U.S. PATENT DOCUMENTS

| | | |
|---|---|---|
| 6,945,975 B2 | 9/2005 | Dalton |
| 6,946,000 B2 | 9/2005 | Senegas et al. |
| 6,949,100 B1 | 9/2005 | Venturini |
| 6,951,561 B2 | 10/2005 | Warren et al. |
| 6,953,477 B2 | 10/2005 | Berry |
| 6,955,691 B2 | 10/2005 | Chae et al. |
| 6,969,404 B2 | 11/2005 | Ferree |
| 6,969,405 B2 | 11/2005 | Suddaby |
| 6,972,035 B2 | 12/2005 | Michelson |
| 6,997,929 B2 | 2/2006 | Manzi et al. |
| 7,004,945 B2 | 2/2006 | Boyd et al. |
| 7,008,431 B2 | 3/2006 | Simonson |
| 7,018,412 B2 | 3/2006 | Ferreira et al. |
| 7,018,415 B1 | 3/2006 | McKay |
| 7,018,416 B2 | 3/2006 | Hanson et al. |
| 7,025,746 B2 | 4/2006 | Tal |
| 7,029,473 B2 | 4/2006 | Zucherman et al. |
| 7,037,339 B2 | 5/2006 | Houfburg et al. |
| 7,041,107 B2 | 5/2006 | Pohjonen et al. |
| 7,048,736 B2 | 5/2006 | Robinson et al. |
| 7,060,068 B2 | 6/2006 | Tromanhauser et al. |
| 7,063,701 B2 | 6/2006 | Michelson |
| 7,063,702 B2 | 6/2006 | Michelson |
| 7,066,960 B1 | 6/2006 | Dickman |
| 7,066,961 B2 | 6/2006 | Michelson |
| 7,070,601 B2 | 7/2006 | Culbert et al. |
| 7,074,203 B1 | 7/2006 | Johanson et al. |
| 7,083,650 B2 | 8/2006 | Moskowitz et al. |
| 7,087,083 B2 | 8/2006 | Pasquet et al. |
| 7,094,239 B1 | 8/2006 | Michelson |
| 7,094,257 B2 | 8/2006 | Mujwid et al. |
| 7,094,258 B2 | 8/2006 | Lambrecht et al. |
| 7,101,375 B2 | 9/2006 | Zucherman et al. |
| 7,114,501 B2 | 10/2006 | Johnson et al. |
| 7,118,572 B2 | 10/2006 | Bramlet et al. |
| 7,118,579 B2 | 10/2006 | Michelson |
| 7,118,598 B2 | 10/2006 | Michelson |
| 7,128,760 B2 | 10/2006 | Michelson |
| 7,153,305 B2 | 12/2006 | Johnson et al. |
| D536,096 S | 1/2007 | Hoogland et al. |
| 7,156,876 B2 | 1/2007 | Moumene et al. |
| 7,163,558 B2 | 1/2007 | Senegas et al. |
| 7,172,612 B2 | 2/2007 | Ishikawa |
| 7,179,294 B2 | 2/2007 | Eisermann et al. |
| 7,201,751 B2 | 4/2007 | Zucherman et al. |
| 7,211,112 B2 | 5/2007 | Baynham et al. |
| 7,217,293 B2 | 5/2007 | Branch |
| 7,220,280 B2 | 5/2007 | Kast et al. |
| 7,223,292 B2 | 5/2007 | Messerli et al. |
| 7,226,481 B2 | 6/2007 | Kuslich |
| 7,226,483 B2 | 6/2007 | Gerber et al. |
| 7,235,101 B2 | 6/2007 | Berry et al. |
| 7,238,204 B2 | 7/2007 | Le Couedic et al. |
| 7,267,683 B2 | 9/2007 | Sharkey et al. |
| 7,282,061 B2 | 10/2007 | Sharkey et al. |
| 7,300,440 B2 | 11/2007 | Zdeblick |
| 7,306,628 B2 | 12/2007 | Zucherman et al. |
| 7,309,357 B2 | 12/2007 | Kim |
| 7,326,211 B2 | 2/2008 | Padget et al. |
| 7,326,248 B2 | 2/2008 | Michelson |
| 7,335,203 B2 | 2/2008 | Winslow et al. |
| 7,361,140 B2 | 4/2008 | Ries et al. |
| 7,371,238 B2 | 5/2008 | Soboleski et al. |
| 7,377,942 B2 | 5/2008 | Berry |
| 7,400,930 B2 | 7/2008 | Sharkey et al. |
| 7,410,501 B2 | 8/2008 | Michelson |
| 7,413,576 B2 | 8/2008 | Sybert et al. |
| 7,422,594 B2 | 9/2008 | Zander |
| 7,434,325 B2 | 10/2008 | Foley et al. |
| 7,445,636 B2 | 11/2008 | Michelson |
| 7,445,637 B2 | 11/2008 | Taylor |
| D584,812 S | 1/2009 | Ries |
| 7,473,256 B2 | 1/2009 | Assell et al. |
| 7,473,268 B2 | 1/2009 | Zucherman et al. |
| 7,476,251 B2 | 1/2009 | Zucherman et al. |
| 7,488,326 B2 | 2/2009 | Elliott |
| 7,503,933 B2 | 3/2009 | Michelson |
| 7,507,241 B2 | 3/2009 | Levy et al. |
| 7,517,363 B2 | 4/2009 | Rogers |
| 7,520,888 B2 | 4/2009 | Trieu |
| 7,547,317 B2 | 6/2009 | Cragg |
| 7,556,629 B2 | 7/2009 | von Hoffmann et al. |
| 7,556,651 B2 | 7/2009 | Humphreys et al. |
| 7,569,054 B2 | 8/2009 | Michelson |
| 7,569,074 B2 | 8/2009 | Eiserman et al. |
| 7,588,574 B2 | 9/2009 | Assell et al. |
| 7,618,458 B2 | 11/2009 | Biedermann et al. |
| 7,621,950 B1 | 11/2009 | Globerman et al. |
| 7,621,960 B2 | 11/2009 | Boyd et al. |
| 7,625,378 B2 | 12/2009 | Foley |
| 7,641,657 B2 | 1/2010 | Cragg |
| 7,641,670 B2 | 1/2010 | Davison et al. |
| 7,647,123 B2 | 1/2010 | Sharkey et al. |
| 7,648,523 B2 | 1/2010 | Mirkovic et al. |
| 7,670,354 B2 | 3/2010 | Davison et al. |
| 7,674,273 B2 | 3/2010 | Davison et al. |
| 7,682,370 B2 | 3/2010 | Pagliuca et al. |
| 7,691,120 B2 | 4/2010 | Shluzas et al. |
| 7,691,147 B2 | 4/2010 | Gutlin et al. |
| 7,699,878 B2 | 4/2010 | Pavlov et al. |
| 7,703,727 B2 | 4/2010 | Selness |
| 7,717,944 B2 | 5/2010 | Foley et al. |
| 7,722,530 B2 | 5/2010 | Davison |
| 7,722,612 B2 | 5/2010 | Sala et al. |
| 7,722,674 B1 | 5/2010 | Grotz |
| 7,727,263 B2 | 6/2010 | Cragg |
| 7,740,633 B2 | 6/2010 | Assell et al. |
| 7,744,599 B2 | 6/2010 | Cragg |
| 7,749,270 B2 | 7/2010 | Peterman |
| 7,762,995 B2 | 7/2010 | Eversull et al. |
| 7,763,025 B2 | 7/2010 | Assell et al. |
| 7,763,055 B2 | 7/2010 | Foley |
| 7,766,930 B2 | 8/2010 | DiPoto et al. |
| 7,771,473 B2 | 8/2010 | Thramann |
| 7,771,479 B2 | 8/2010 | Humphreys et al. |
| 7,785,368 B2 | 8/2010 | Schaller |
| 7,789,914 B2 | 9/2010 | Michelson |
| 7,794,463 B2 | 9/2010 | Cragg |
| 7,799,032 B2 | 9/2010 | Assell et al. |
| 7,799,033 B2 | 9/2010 | Assell et al. |
| 7,799,036 B2 | 9/2010 | Davison et al. |
| 7,799,083 B2 | 9/2010 | Smith et al. |
| D626,233 S | 10/2010 | Cipoletti et al. |
| 7,814,429 B2 | 10/2010 | Buffet et al. |
| 7,819,921 B2 | 10/2010 | Grotz |
| 7,824,410 B2 | 11/2010 | Simonson et al. |
| 7,824,429 B2 | 11/2010 | Culbert et al. |
| 7,824,445 B2 | 11/2010 | Biro et al. |
| 7,837,734 B2 | 11/2010 | Zucherman et al. |
| 7,846,183 B2 | 12/2010 | Blain |
| 7,846,206 B2 | 12/2010 | Oglaza et al. |
| 7,850,695 B2 | 12/2010 | Pagliuca et al. |
| 7,850,733 B2 | 12/2010 | Baynham et al. |
| 7,854,766 B2 | 12/2010 | Moskowitz et al. |
| 7,857,832 B2 | 12/2010 | Culbert et al. |
| 7,857,840 B2 | 12/2010 | Krebs |
| 7,862,590 B2 | 1/2011 | Lim et al. |
| 7,862,595 B2 | 1/2011 | Foley et al. |
| 7,867,259 B2 | 1/2011 | Foley et al. |
| 7,874,980 B2 | 1/2011 | Sonnenschein et al. |
| 7,875,077 B2 | 1/2011 | Humphreys et al. |
| 7,879,098 B1 | 2/2011 | Simmons |
| 7,887,589 B2 | 2/2011 | Glenn et al. |
| 7,892,171 B2 | 2/2011 | Davison et al. |
| 7,892,249 B2 | 2/2011 | Davison et al. |
| 7,901,438 B2 | 3/2011 | Culbert et al. |
| 7,901,459 B2 | 3/2011 | Hodges et al. |
| 7,909,870 B2 | 3/2011 | Kraus |
| 7,922,729 B2 | 4/2011 | Michelson |
| 7,931,689 B2 | 4/2011 | Hochschuler et al. |
| 7,938,832 B2 | 5/2011 | Culbert et al. |
| 7,951,199 B2 | 5/2011 | Miller |
| 7,985,231 B2 | 7/2011 | Sankaran |
| 7,993,403 B2 | 8/2011 | Foley et al. |

(56) References Cited

U.S. PATENT DOCUMENTS

| | | |
|---|---|---|
| 7,998,176 B2 | 8/2011 | Culbert |
| 8,021,424 B2 | 9/2011 | Beger et al. |
| 8,021,426 B2 | 9/2011 | Segal et al. |
| 8,025,697 B2 | 9/2011 | McClellan et al. |
| 8,034,109 B2 | 10/2011 | Zwirkoski |
| 8,043,381 B2 | 10/2011 | Hestad et al. |
| 8,062,375 B2 | 11/2011 | Glerum et al. |
| 8,075,621 B2 | 12/2011 | Michelson |
| 8,109,977 B2 | 2/2012 | Culbert et al. |
| 8,114,088 B2 | 2/2012 | Miller |
| 8,133,232 B2 | 3/2012 | Levy et al. |
| 8,177,812 B2 | 5/2012 | Sankaran |
| 8,192,495 B2 | 6/2012 | Simpson et al. |
| 8,221,501 B2 | 7/2012 | Eisermann et al. |
| 8,221,502 B2 | 7/2012 | Branch |
| 8,231,681 B2 | 7/2012 | Castleman et al. |
| 8,236,058 B2 | 8/2012 | Fabian et al. |
| 8,241,358 B2 | 8/2012 | Butler et al. |
| 8,257,442 B2 | 9/2012 | Edie et al. |
| 8,262,666 B2 | 9/2012 | Baynham et al. |
| 8,262,736 B2 | 9/2012 | Michelson |
| 8,267,939 B2 | 9/2012 | Cipoletti et al. |
| 8,273,128 B2 | 9/2012 | Oh et al. |
| 8,273,129 B2 | 9/2012 | Baynham et al. |
| 8,287,599 B2 | 10/2012 | McGuckin |
| 8,303,663 B2 | 11/2012 | Jimenez et al. |
| 8,317,866 B2 | 11/2012 | Palmatier et al. |
| 8,323,345 B2 | 12/2012 | Sledge |
| 8,328,852 B2 | 12/2012 | Zehavi et al. |
| 8,337,559 B2 | 12/2012 | Hansell et al. |
| 8,353,961 B2 | 1/2013 | McClintock |
| 8,366,777 B2 | 2/2013 | Matthis et al. |
| 8,382,842 B2 | 2/2013 | Greenhalgh et al. |
| 8,394,129 B2 | 3/2013 | Morgenstern Lopez et al. |
| 8,398,713 B2 | 3/2013 | Weiman |
| 8,403,990 B2 | 3/2013 | Dryer et al. |
| 8,409,291 B2 | 4/2013 | Blackwell et al. |
| 8,435,298 B2 | 5/2013 | Weiman |
| 8,454,617 B2 | 6/2013 | Schaller |
| 8,486,148 B2 | 7/2013 | Butler et al. |
| 8,491,659 B2 | 7/2013 | Weiman |
| 8,506,635 B2 | 8/2013 | Palmatier et al. |
| 8,518,087 B2 | 8/2013 | Lopez et al. |
| 8,518,120 B2 | 8/2013 | Glerum et al. |
| 8,551,173 B2 | 10/2013 | Lechmann et al. |
| 8,556,979 B2 | 10/2013 | Glerum et al. |
| 8,568,481 B2 | 10/2013 | Olmos et al. |
| 8,579,977 B2 | 11/2013 | Fabian |
| 8,579,981 B2 | 11/2013 | Lim |
| 8,591,585 B2 | 11/2013 | McLaughlin et al. |
| 8,597,333 B2 | 12/2013 | Morgenstern Lopez et al. |
| 8,628,576 B2 | 1/2014 | Triplett et al. |
| 8,628,578 B2 | 1/2014 | Miller et al. |
| 8,632,595 B2 | 1/2014 | Weiman |
| 8,663,329 B2 | 3/2014 | Ernst |
| 8,668,740 B2 | 3/2014 | Rhoda et al. |
| 8,679,183 B2 | 3/2014 | Glerum et al. |
| 8,685,098 B2 | 4/2014 | Glerum et al. |
| 8,696,751 B2 | 4/2014 | Ashley et al. |
| 8,709,086 B2 | 4/2014 | Glerum et al. |
| 8,715,351 B1 | 5/2014 | Pinto |
| 8,721,723 B2 | 5/2014 | Hansell et al. |
| 8,753,398 B2 | 6/2014 | Gordon et al. |
| 8,771,360 B2 | 7/2014 | Jimenez et al. |
| 8,778,025 B2 | 7/2014 | Ragab et al. |
| 8,795,366 B2 | 8/2014 | Varela |
| 8,828,085 B1 | 9/2014 | Jensen |
| 8,845,731 B2 | 9/2014 | Weiman |
| 8,845,732 B2 | 9/2014 | Weiman |
| 8,845,734 B2 | 9/2014 | Weiman |
| 8,852,242 B2 | 10/2014 | Morgenstern Lopez et al. |
| 8,852,243 B2 | 10/2014 | Morgenstern Lopez et al. |
| 8,852,279 B2 | 10/2014 | Weiman |
| 8,864,833 B2 | 10/2014 | Glerum et al. |
| 8,888,853 B2 | 11/2014 | Glerum et al. |
| 8,888,854 B2 | 11/2014 | Glerum et al. |
| 8,900,307 B2 | 12/2014 | Hawkins et al. |
| 8,936,641 B2 | 1/2015 | Cain |
| 8,940,052 B2 | 1/2015 | Lechmann et al. |
| 8,979,860 B2 | 3/2015 | Voellmicke et al. |
| 9,095,446 B2 | 8/2015 | Landry et al. |
| 9,095,447 B2 | 8/2015 | Barreiro et al. |
| 9,277,928 B2 | 3/2016 | Morgenstern Lopez |
| 2001/0012950 A1 | 8/2001 | Nishtala et al. |
| 2001/0027320 A1 | 10/2001 | Sasso |
| 2001/0037126 A1 | 11/2001 | Stack et al. |
| 2001/0039452 A1 | 11/2001 | Zucherman et al. |
| 2001/0049529 A1 | 12/2001 | Cachia et al. |
| 2001/0049530 A1 | 12/2001 | Culbert et al. |
| 2002/0001476 A1 | 1/2002 | Nagamine et al. |
| 2002/0010070 A1 | 1/2002 | Cales et al. |
| 2002/0032462 A1 | 3/2002 | Houser et al. |
| 2002/0055740 A1 | 5/2002 | Lieberman |
| 2002/0068976 A1 | 6/2002 | Jackson |
| 2002/0068977 A1 | 6/2002 | Jackson |
| 2002/0087152 A1 | 7/2002 | Mikus et al. |
| 2002/0091387 A1 | 7/2002 | Hoogland |
| 2002/0120335 A1 | 8/2002 | Angelucci et al. |
| 2002/0128715 A1 | 9/2002 | Bryan et al. |
| 2002/0128716 A1 | 9/2002 | Cohen et al. |
| 2002/0138146 A1 | 9/2002 | Jackson |
| 2002/0143331 A1 | 10/2002 | Zucherman et al. |
| 2002/0143334 A1 | 10/2002 | Hoffmann et al. |
| 2002/0143335 A1 | 10/2002 | von Hoffmann et al. |
| 2002/0151895 A1 | 10/2002 | Soboleski et al. |
| 2002/0151976 A1 | 10/2002 | Foley et al. |
| 2002/0161444 A1 | 10/2002 | Choi |
| 2002/0165612 A1 | 11/2002 | Gerber et al. |
| 2002/0183848 A1 | 12/2002 | Ray et al. |
| 2003/0004575 A1 | 1/2003 | Erickson |
| 2003/0004576 A1 | 1/2003 | Thalgott |
| 2003/0023305 A1 | 1/2003 | McKay |
| 2003/0028250 A1 | 2/2003 | Reiley et al. |
| 2003/0040799 A1 | 2/2003 | Boyd et al. |
| 2003/0063582 A1 | 4/2003 | Culbert |
| 2003/0065330 A1 | 4/2003 | Zucherman et al. |
| 2003/0065396 A1 | 4/2003 | Michelson |
| 2003/0069582 A1 | 4/2003 | Culbert et al. |
| 2003/0078667 A1 | 4/2003 | Manasas et al. |
| 2003/0083688 A1 | 5/2003 | Simonson |
| 2003/0130739 A1 | 7/2003 | Gerbec et al. |
| 2003/0135275 A1* | 7/2003 | Garcia ............... A61B 17/1671 623/17.11 |
| 2003/0139648 A1 | 7/2003 | Foley et al. |
| 2003/0139812 A1* | 7/2003 | Garcia ............... A61B 17/1671 623/17.11 |
| 2003/0139813 A1 | 7/2003 | Messerli et al. |
| 2003/0153874 A1 | 8/2003 | Tal |
| 2003/0187431 A1 | 10/2003 | Simonson |
| 2003/0204261 A1 | 10/2003 | Eisermann |
| 2003/0208122 A1 | 11/2003 | Melkent et al. |
| 2003/0208220 A1 | 11/2003 | Worley et al. |
| 2003/0220643 A1 | 11/2003 | Ferree |
| 2003/0229350 A1 | 12/2003 | Kay |
| 2003/0233102 A1 | 12/2003 | Nakamura et al. |
| 2003/0233145 A1 | 12/2003 | Landry et al. |
| 2004/0002761 A1 | 1/2004 | Rogers |
| 2004/0006391 A1 | 1/2004 | Reiley |
| 2004/0008949 A1 | 1/2004 | Liu et al. |
| 2004/0019359 A1 | 1/2004 | Worley et al. |
| 2004/0024463 A1 | 2/2004 | Thomas et al. |
| 2004/0030387 A1 | 2/2004 | Landry et al. |
| 2004/0049190 A1 | 3/2004 | Biedermann et al. |
| 2004/0049223 A1 | 3/2004 | Nishtala et al. |
| 2004/0054412 A1 | 3/2004 | Gerbec et al. |
| 2004/0059339 A1 | 3/2004 | Roehm, III et al. |
| 2004/0059350 A1 | 3/2004 | Gordon et al. |
| 2004/0064144 A1 | 4/2004 | Johnson et al. |
| 2004/0073310 A1 | 4/2004 | Moumene |
| 2004/0087947 A1 | 5/2004 | Lim |
| 2004/0088055 A1 | 5/2004 | Hanson et al. |
| 2004/0097924 A1 | 5/2004 | Lambrecht et al. |
| 2004/0097941 A1 | 5/2004 | Weiner et al. |
| 2004/0097973 A1 | 5/2004 | Loshakove et al. |

(56) References Cited

U.S. PATENT DOCUMENTS

| | | |
|---|---|---|
| 2004/0106925 A1 | 6/2004 | Culbert |
| 2004/0127906 A1 | 7/2004 | Culbert et al. |
| 2004/0127991 A1 | 7/2004 | Ferree |
| 2004/0133280 A1 | 7/2004 | Trieu |
| 2004/0143284 A1 | 7/2004 | Chin |
| 2004/0143734 A1 | 7/2004 | Buer et al. |
| 2004/0147877 A1 | 7/2004 | Heuser |
| 2004/0147950 A1 | 7/2004 | Mueller et al. |
| 2004/0153065 A1 | 8/2004 | Lim |
| 2004/0153156 A1 | 8/2004 | Cohen et al. |
| 2004/0158258 A1 | 8/2004 | Bonati et al. |
| 2004/0162617 A1 | 8/2004 | Zucherman et al. |
| 2004/0162618 A1 | 8/2004 | Mujwid et al. |
| 2004/0172133 A1 | 9/2004 | Gerber et al. |
| 2004/0186471 A1 | 9/2004 | Trieu |
| 2004/0186482 A1 | 9/2004 | Kolb et al. |
| 2004/0186570 A1 | 9/2004 | Rapp |
| 2004/0186577 A1 | 9/2004 | Ferree |
| 2004/0193277 A1 | 9/2004 | Long |
| 2004/0199162 A1 | 10/2004 | von Hoffmann et al. |
| 2004/0215343 A1 | 10/2004 | Hochschuler et al. |
| 2004/0215344 A1 | 10/2004 | Hochschuler et al. |
| 2004/0220580 A1 | 11/2004 | Johnson et al. |
| 2004/0225292 A1 | 11/2004 | Sasso et al. |
| 2004/0225361 A1 | 11/2004 | Glenn et al. |
| 2004/0230309 A1 | 11/2004 | DiMauro |
| 2004/0243239 A1 | 12/2004 | Taylor |
| 2004/0249466 A1 | 12/2004 | Liu et al. |
| 2004/0254575 A1 | 12/2004 | Obenchain et al. |
| 2004/0260297 A1 | 12/2004 | Padget et al. |
| 2004/0266257 A1 | 12/2004 | Ries et al. |
| 2005/0010292 A1 | 1/2005 | Carrasco |
| 2005/0019365 A1 | 1/2005 | Frauchiger et al. |
| 2005/0033289 A1 | 2/2005 | Warren et al. |
| 2005/0033434 A1 | 2/2005 | Berry |
| 2005/0038515 A1 | 2/2005 | Kunzler |
| 2005/0043796 A1 | 2/2005 | Grant et al. |
| 2005/0065610 A1 | 3/2005 | Pisharodi |
| 2005/0090443 A1 | 4/2005 | Fallin et al. |
| 2005/0090833 A1 | 4/2005 | Di Poto |
| 2005/0102202 A1 | 5/2005 | Linden et al. |
| 2005/0113916 A1 | 5/2005 | Branch |
| 2005/0113917 A1 | 5/2005 | Chae et al. |
| 2005/0113927 A1 | 5/2005 | Malek |
| 2005/0118550 A1 | 6/2005 | Turri |
| 2005/0119657 A1 | 6/2005 | Goldsmith |
| 2005/0125062 A1 | 6/2005 | Biedermann et al. |
| 2005/0130929 A1 | 6/2005 | Boyd |
| 2005/0131406 A1 | 6/2005 | Reiley et al. |
| 2005/0131409 A1 | 6/2005 | Chervitz et al. |
| 2005/0131411 A1 | 6/2005 | Culbert et al. |
| 2005/0131538 A1 | 6/2005 | Chervitz et al. |
| 2005/0137595 A1 | 6/2005 | von Hoffmann et al. |
| 2005/0143734 A1 | 6/2005 | Cachia et al. |
| 2005/0149030 A1 | 7/2005 | Serhan |
| 2005/0154467 A1 | 7/2005 | Peterman et al. |
| 2005/0165398 A1 | 7/2005 | Reiley |
| 2005/0165485 A1 | 7/2005 | Trieu |
| 2005/0171552 A1 | 8/2005 | Johnson et al. |
| 2005/0171608 A1 | 8/2005 | Peterman et al. |
| 2005/0171610 A1 | 8/2005 | Humphreys et al. |
| 2005/0177240 A1 | 8/2005 | Blain |
| 2005/0182414 A1 | 8/2005 | Manzi et al. |
| 2005/0182418 A1 | 8/2005 | Boyd et al. |
| 2005/0187558 A1 | 8/2005 | Johnson et al. |
| 2005/0187559 A1 | 8/2005 | Raymond et al. |
| 2005/0203512 A1 | 9/2005 | Hawkins et al. |
| 2005/0216026 A1 | 9/2005 | Culbert |
| 2005/0222681 A1 | 10/2005 | Richley et al. |
| 2005/0251142 A1 | 11/2005 | von Hoffmann et al. |
| 2005/0256525 A1 | 11/2005 | Warren et al. |
| 2005/0256576 A1 | 11/2005 | Moskowitz et al. |
| 2005/0261769 A1 | 11/2005 | Moskowitz et al. |
| 2005/0278026 A1 | 12/2005 | Gordon et al. |
| 2005/0283238 A1 | 12/2005 | Reiley |
| 2006/0004326 A1 | 1/2006 | Collins et al. |
| 2006/0004457 A1 | 1/2006 | Collins et al. |
| 2006/0004458 A1 | 1/2006 | Collins et al. |
| 2006/0009778 A1 | 1/2006 | Collins et al. |
| 2006/0009779 A1 | 1/2006 | Collins et al. |
| 2006/0009851 A1 | 1/2006 | Collins et al. |
| 2006/0015105 A1 | 1/2006 | Warren et al. |
| 2006/0020284 A1 | 1/2006 | Foley et al. |
| 2006/0030872 A1 | 2/2006 | Culbert et al. |
| 2006/0036246 A1 | 2/2006 | Carl et al. |
| 2006/0036256 A1 | 2/2006 | Carl et al. |
| 2006/0036259 A1 | 2/2006 | Carl et al. |
| 2006/0036323 A1 | 2/2006 | Carl et al. |
| 2006/0036324 A1 | 2/2006 | Sachs et al. |
| 2006/0041314 A1 | 2/2006 | Millard |
| 2006/0058790 A1 | 3/2006 | Carl et al. |
| 2006/0058807 A1 | 3/2006 | Landry et al. |
| 2006/0058876 A1 | 3/2006 | McKinley |
| 2006/0058880 A1 | 3/2006 | Wysocki |
| 2006/0079908 A1 | 4/2006 | Lieberman |
| 2006/0084977 A1 | 4/2006 | Lieberman |
| 2006/0084988 A1 | 4/2006 | Kim |
| 2006/0085010 A1 | 4/2006 | Lieberman |
| 2006/0100706 A1 | 5/2006 | Shadduck et al. |
| 2006/0100707 A1 | 5/2006 | Stinson et al. |
| 2006/0106381 A1 | 5/2006 | Ferree et al. |
| 2006/0119629 A1 | 6/2006 | An et al. |
| 2006/0122609 A1 | 6/2006 | Mirkovic et al. |
| 2006/0122610 A1 | 6/2006 | Culbert et al. |
| 2006/0122701 A1 | 6/2006 | Kiester |
| 2006/0122703 A1 | 6/2006 | Aebi et al. |
| 2006/0129244 A1 | 6/2006 | Ensign |
| 2006/0136062 A1 | 6/2006 | DiNello et al. |
| 2006/0142765 A9 | 6/2006 | Dixon et al. |
| 2006/0142776 A1 | 6/2006 | Iwanari |
| 2006/0142858 A1 | 6/2006 | Colleran et al. |
| 2006/0161166 A1 | 7/2006 | Johnson et al. |
| 2006/0178743 A1 | 8/2006 | Carter |
| 2006/0195103 A1 | 8/2006 | Padget et al. |
| 2006/0206207 A1 | 9/2006 | Dryer et al. |
| 2006/0217711 A1 | 9/2006 | Stevens et al. |
| 2006/0229629 A1 | 10/2006 | Manzi et al. |
| 2006/0235403 A1 | 10/2006 | Blain |
| 2006/0235412 A1 | 10/2006 | Blain |
| 2006/0235531 A1 | 10/2006 | Buettner-Janz |
| 2006/0247634 A1 | 11/2006 | Warner et al. |
| 2006/0253201 A1 | 11/2006 | McLuen |
| 2006/0265075 A1 | 11/2006 | Baumgartner et al. |
| 2006/0265077 A1 | 11/2006 | Zwirkoski |
| 2006/0276899 A1 | 12/2006 | Zipnick et al. |
| 2006/0276901 A1 | 12/2006 | Zipnick et al. |
| 2006/0276902 A1 | 12/2006 | Boyer, II et al. |
| 2006/0293662 A1 | 12/2006 | Boyer et al. |
| 2006/0293663 A1 | 12/2006 | Walkenhorst et al. |
| 2007/0010826 A1 | 1/2007 | Rhoda |
| 2007/0010886 A1 | 1/2007 | Banick et al. |
| 2007/0016191 A1 | 1/2007 | Culbert et al. |
| 2007/0032790 A1 | 2/2007 | Aschmann et al. |
| 2007/0055236 A1 | 3/2007 | Hudgins et al. |
| 2007/0055377 A1 | 3/2007 | Hanson et al. |
| 2007/0067035 A1 | 3/2007 | Falahee |
| 2007/0073399 A1 | 3/2007 | Zipnick et al. |
| 2007/0118132 A1 | 5/2007 | Culbert et al. |
| 2007/0118222 A1 | 5/2007 | Lang |
| 2007/0118223 A1 | 5/2007 | Allard et al. |
| 2007/0123868 A1 | 5/2007 | Culbert et al. |
| 2007/0123891 A1 | 5/2007 | Ries et al. |
| 2007/0123892 A1 | 5/2007 | Ries et al. |
| 2007/0129730 A1 | 6/2007 | Woods et al. |
| 2007/0149978 A1 | 6/2007 | Shezifi et al. |
| 2007/0162005 A1 | 7/2007 | Peterson et al. |
| 2007/0168036 A1 | 7/2007 | Ainsworth et al. |
| 2007/0173939 A1 | 7/2007 | Kim et al. |
| 2007/0173940 A1 | 7/2007 | Hestad et al. |
| 2007/0178222 A1 | 8/2007 | Storey et al. |
| 2007/0191959 A1 | 8/2007 | Hartmann et al. |
| 2007/0198089 A1 | 8/2007 | Moskowitz et al. |
| 2007/0203491 A1 | 8/2007 | Pasquet et al. |
| 2007/0208423 A1 | 9/2007 | Messerli et al. |

(56) References Cited

U.S. PATENT DOCUMENTS

| | | |
|---|---|---|
| 2007/0219634 A1 | 9/2007 | Greenhalgh et al. |
| 2007/0233083 A1 | 10/2007 | Abdou |
| 2007/0233089 A1 | 10/2007 | DiPoto et al. |
| 2007/0233244 A1 | 10/2007 | Lopez et al. |
| 2007/0270954 A1 | 11/2007 | Wu |
| 2007/0270968 A1 | 11/2007 | Baynham et al. |
| 2007/0276375 A1 | 11/2007 | Rapp |
| 2007/0282449 A1 | 12/2007 | de Villiers et al. |
| 2007/0299521 A1 | 12/2007 | Glenn |
| 2008/0009877 A1 | 1/2008 | Sankaran et al. |
| 2008/0015701 A1 | 1/2008 | Garcia et al. |
| 2008/0021556 A1 | 1/2008 | Edie |
| 2008/0021558 A1 | 1/2008 | Thramann |
| 2008/0027550 A1 | 1/2008 | Link et al. |
| 2008/0033440 A1 | 2/2008 | Moskowitz et al. |
| 2008/0058598 A1 | 3/2008 | Ries et al. |
| 2008/0058944 A1 | 3/2008 | Duplessis et al. |
| 2008/0065219 A1 | 3/2008 | Dye |
| 2008/0077148 A1 | 3/2008 | Ries et al. |
| 2008/0082172 A1 | 4/2008 | Jackson |
| 2008/0082173 A1 | 4/2008 | Delurio et al. |
| 2008/0097436 A1 | 4/2008 | Culbert et al. |
| 2008/0108996 A1 | 5/2008 | Padget et al. |
| 2008/0132934 A1 | 6/2008 | Reilly |
| 2008/0140207 A1 | 6/2008 | Olmos |
| 2008/0147193 A1 | 6/2008 | Matthis et al. |
| 2008/0154377 A1 | 6/2008 | Voellmicke et al. |
| 2008/0161927 A1 | 7/2008 | Savage |
| 2008/0167657 A1 | 7/2008 | Greenhalgh |
| 2008/0177388 A1 | 7/2008 | Patterson et al. |
| 2008/0183204 A1 | 7/2008 | Greenhalgh et al. |
| 2008/0195209 A1 | 8/2008 | Garcia et al. |
| 2008/0243251 A1 | 10/2008 | Stad et al. |
| 2008/0243254 A1 | 10/2008 | Butler |
| 2008/0249622 A1* | 10/2008 | Gray .................. A61F 2/4455 606/86 A |
| 2008/0255618 A1 | 10/2008 | Fisher et al. |
| 2008/0262619 A1 | 10/2008 | Ray |
| 2008/0281425 A1 | 11/2008 | Thalgott |
| 2008/0287981 A1 | 11/2008 | Culbert et al. |
| 2008/0287997 A1 | 11/2008 | Altarac et al. |
| 2008/0300685 A1 | 12/2008 | Carls et al. |
| 2008/0306537 A1 | 12/2008 | Culbert |
| 2009/0005873 A1 | 1/2009 | Slivka et al. |
| 2009/0030423 A1 | 1/2009 | Puno |
| 2009/0054991 A1 | 2/2009 | Biyani |
| 2009/0069813 A1 | 3/2009 | von Hoffmann et al. |
| 2009/0076610 A1 | 3/2009 | Afzal |
| 2009/0099568 A1 | 4/2009 | Lowry et al. |
| 2009/0105712 A1 | 4/2009 | Dauster |
| 2009/0105745 A1 | 4/2009 | Culbert |
| 2009/0112320 A1 | 4/2009 | Kraus |
| 2009/0112324 A1 | 4/2009 | Refai et al. |
| 2009/0131986 A1 | 5/2009 | Lee et al. |
| 2009/0149857 A1 | 6/2009 | Culbert et al. |
| 2009/0164020 A1 | 6/2009 | Janowski |
| 2009/0177284 A1 | 7/2009 | Rogers et al. |
| 2009/0182429 A1 | 7/2009 | Humphreys et al. |
| 2009/0198339 A1 | 8/2009 | Kleiner |
| 2009/0222096 A1 | 9/2009 | Trieu |
| 2009/0222099 A1 | 9/2009 | Liu et al. |
| 2009/0222100 A1 | 9/2009 | Cipoletti et al. |
| 2009/0234398 A1 | 9/2009 | Chirico et al. |
| 2009/0240335 A1 | 9/2009 | Arcenio et al. |
| 2009/0248159 A1 | 10/2009 | Aflatoon |
| 2009/0275890 A1 | 11/2009 | Leibowitz et al. |
| 2009/0292361 A1 | 11/2009 | Lopez |
| 2010/0016905 A1 | 1/2010 | Greenhalgh et al. |
| 2010/0040332 A1 | 2/2010 | Van Den Meersschaut et al. |
| 2010/0076492 A1 | 3/2010 | Warner et al. |
| 2010/0076559 A1 | 3/2010 | Bagga |
| 2010/0082109 A1 | 4/2010 | Greenhalgh et al. |
| 2010/0114105 A1 | 5/2010 | Butters |
| 2010/0114147 A1 | 5/2010 | Biyani |
| 2010/0174314 A1 | 7/2010 | Mirkovic et al. |
| 2010/0179594 A1 | 7/2010 | Theofilos et al. |
| 2010/0191336 A1 | 7/2010 | Greenhalgh |
| 2010/0204795 A1 | 8/2010 | Greenhalgh |
| 2010/0211176 A1 | 8/2010 | Greenhalgh |
| 2010/0234956 A1 | 9/2010 | Attia et al. |
| 2010/0262240 A1 | 10/2010 | Chavatte et al. |
| 2010/0268231 A1 | 10/2010 | Kuslich et al. |
| 2010/0286783 A1 | 11/2010 | Lechmann et al. |
| 2010/0292700 A1 | 11/2010 | Ries |
| 2010/0298938 A1 | 11/2010 | Humphreys et al. |
| 2010/0324607 A1 | 12/2010 | Davis |
| 2010/0331891 A1 | 12/2010 | Culbert et al. |
| 2011/0004308 A1 | 1/2011 | Marino et al. |
| 2011/0004310 A1 | 1/2011 | Michelson |
| 2011/0015747 A1 | 1/2011 | McManus et al. |
| 2011/0029082 A1 | 2/2011 | Hall |
| 2011/0035011 A1 | 2/2011 | Cain |
| 2011/0054538 A1 | 3/2011 | Zehavi et al. |
| 2011/0071527 A1 | 3/2011 | Nelson et al. |
| 2011/0093074 A1 | 4/2011 | Glerum et al. |
| 2011/0098531 A1 | 4/2011 | To |
| 2011/0098628 A1 | 4/2011 | Yeung et al. |
| 2011/0130835 A1 | 6/2011 | Ashley et al. |
| 2011/0130838 A1 | 6/2011 | Morgenstern Lopez |
| 2011/0144753 A1 | 6/2011 | Marchek et al. |
| 2011/0153020 A1 | 6/2011 | Abdelgany et al. |
| 2011/0172716 A1 | 7/2011 | Glerum |
| 2011/0172774 A1 | 7/2011 | Varela |
| 2011/0238072 A1 | 9/2011 | Tyndall |
| 2011/0270261 A1 | 11/2011 | Mast et al. |
| 2011/0282453 A1 | 11/2011 | Greenhalgh et al. |
| 2011/0301711 A1 | 12/2011 | Palmatier et al. |
| 2011/0301712 A1 | 12/2011 | Palmatier et al. |
| 2011/0307010 A1 | 12/2011 | Pradhan |
| 2011/0313465 A1 | 12/2011 | Warren et al. |
| 2012/0004726 A1 | 1/2012 | Greenhalgh et al. |
| 2012/0004732 A1 | 1/2012 | Goel et al. |
| 2012/0022654 A1 | 1/2012 | Farris et al. |
| 2012/0029636 A1 | 2/2012 | Ragab et al. |
| 2012/0059474 A1 | 3/2012 | Weiman |
| 2012/0059475 A1 | 3/2012 | Weiman |
| 2012/0071977 A1 | 3/2012 | Oglaza et al. |
| 2012/0071980 A1 | 3/2012 | Purcell et al. |
| 2012/0083889 A1 | 4/2012 | Purcell et al. |
| 2012/0123546 A1 | 5/2012 | Medina |
| 2012/0150304 A1 | 6/2012 | Glerum et al. |
| 2012/0150305 A1 | 6/2012 | Glerum et al. |
| 2012/0158146 A1 | 6/2012 | Glerum et al. |
| 2012/0158147 A1 | 6/2012 | Glerum et al. |
| 2012/0158148 A1 | 6/2012 | Glerum et al. |
| 2012/0185049 A1 | 7/2012 | Varela |
| 2012/0197403 A1 | 8/2012 | Merves |
| 2012/0203290 A1 | 8/2012 | Warren et al. |
| 2012/0203347 A1 | 8/2012 | Glerum et al. |
| 2012/0215262 A1 | 8/2012 | Culbert et al. |
| 2012/0226357 A1 | 9/2012 | Varela |
| 2012/0232658 A1 | 9/2012 | Morgenstern Lopez et al. |
| 2012/0277795 A1 | 11/2012 | von Hoffmann et al. |
| 2012/0290090 A1 | 11/2012 | Glerum et al. |
| 2012/0290097 A1 | 11/2012 | Cipoletti et al. |
| 2012/0310350 A1 | 12/2012 | Farris et al. |
| 2012/0310352 A1 | 12/2012 | DiMauro et al. |
| 2012/0323328 A1 | 12/2012 | Weiman |
| 2012/0330421 A1 | 12/2012 | Weiman |
| 2012/0330422 A1 | 12/2012 | Weiman |
| 2013/0006361 A1 | 1/2013 | Glerum et al. |
| 2013/0023993 A1 | 1/2013 | Weiman |
| 2013/0023994 A1 | 1/2013 | Glerum |
| 2013/0030536 A1 | 1/2013 | Rhoda et al. |
| 2013/0085572 A1 | 4/2013 | Glerum et al. |
| 2013/0085574 A1 | 4/2013 | Sledge |
| 2013/0116791 A1 | 5/2013 | Theofilos |
| 2013/0123924 A1 | 5/2013 | Butler et al. |
| 2013/0123927 A1 | 5/2013 | Malandain |
| 2013/0138214 A1 | 5/2013 | Greenhalgh et al. |
| 2013/0144387 A1 | 6/2013 | Walker et al. |
| 2013/0144388 A1 | 6/2013 | Emery et al. |
| 2013/0158663 A1 | 6/2013 | Miller et al. |
| 2013/0158664 A1 | 6/2013 | Palmatier et al. |

(56) References Cited

U.S. PATENT DOCUMENTS

| | | |
|---|---|---|
| 2013/0158667 A1 | 6/2013 | Tabor et al. |
| 2013/0158668 A1 | 6/2013 | Nichols et al. |
| 2013/0158669 A1 | 6/2013 | Sungarian et al. |
| 2013/0173004 A1 | 7/2013 | Greenhalgh et al. |
| 2013/0190876 A1 | 7/2013 | Drochner et al. |
| 2013/0190877 A1 | 7/2013 | Medina |
| 2013/0204371 A1 | 8/2013 | McLuen et al. |
| 2013/0211525 A1 | 8/2013 | McLuen et al. |
| 2013/0211526 A1 | 8/2013 | Alheidt et al. |
| 2013/0310939 A1 | 11/2013 | Fabian et al. |
| 2014/0039622 A1 | 2/2014 | Glerum et al. |
| 2014/0046333 A1 | 2/2014 | Johnson et al. |
| 2014/0058513 A1 | 2/2014 | Gahman et al. |
| 2014/0067073 A1 | 3/2014 | Hauck |
| 2014/0114423 A1 | 4/2014 | Suedkamp et al. |
| 2014/0128977 A1 | 5/2014 | Glerum et al. |
| 2014/0135934 A1 | 5/2014 | Hansell et al. |
| 2014/0142706 A1 | 5/2014 | Hansell et al. |
| 2014/0163683 A1 | 6/2014 | Seifert et al. |
| 2014/0172106 A1 | 6/2014 | To et al. |
| 2014/0180421 A1 | 6/2014 | Glerum et al. |
| 2014/0249629 A1 | 9/2014 | Moskowitz et al. |
| 2014/0249630 A1 | 9/2014 | Weiman |
| 2014/0257484 A1 | 9/2014 | Flower et al. |
| 2014/0257486 A1 | 9/2014 | Alheidt |
| 2014/0277204 A1 | 9/2014 | Sandhu |
| 2014/0303731 A1 | 10/2014 | Glerum et al. |
| 2014/0303732 A1 | 10/2014 | Rhoda et al. |
| 2014/0324171 A1 | 10/2014 | Glerum et al. |
| 2015/0045894 A1 | 2/2015 | Hawkins et al. |
| 2015/0094610 A1 | 4/2015 | Morgenstern Lopez et al. |
| 2015/0094812 A1 | 4/2015 | Cain |
| 2015/0094813 A1 | 4/2015 | Lechmann et al. |
| 2015/0112398 A1 | 4/2015 | Morgenstern Lopez et al. |
| 2015/0157470 A1 | 6/2015 | Voellmicke et al. |
| 2016/0367265 A1 | 12/2016 | Morgenstern Lopez |

FOREIGN PATENT DOCUMENTS

| | | |
|---|---|---|
| CN | 101909548 A | 12/2010 |
| DE | 2804936 | 8/1979 |
| DE | 3023353 | 4/1981 |
| DE | 3911610 | 10/1990 |
| DE | 4012622 | 7/1997 |
| DE | 19832798 | 11/1999 |
| DE | 20101793 | 5/2001 |
| DE | 202008001079 | 3/2008 |
| EP | 077159 | 4/1983 |
| EP | 0260044 | 3/1988 |
| EP | 282161 | 9/1988 |
| EP | 0433717 | 6/1991 |
| EP | 0525352 | 2/1993 |
| EP | 0611557 | 8/1994 |
| EP | 0625336 | 11/1994 |
| EP | 678489 | 10/1995 |
| EP | 0270704 | 6/1998 |
| EP | 1046376 | 4/2000 |
| EP | 0853929 | 9/2002 |
| EP | 1290985 | 3/2003 |
| EP | 1378205 | 7/2003 |
| EP | 1374784 | 1/2004 |
| EP | 1532949 | 5/2005 |
| EP | 1541096 | 6/2005 |
| EP | 1683593 | 7/2006 |
| EP | 1698305 B1 | 8/2007 |
| EP | 1843723 B1 | 3/2010 |
| EP | 2368529 | 9/2011 |
| EP | 2237748 B1 | 9/2012 |
| EP | 1845874 | 10/2012 |
| EP | 2764851 | 8/2014 |
| FR | 2649311 | 1/1991 |
| FR | 2699065 | 12/1992 |
| FR | 2728778 | 12/1994 |
| FR | 2718635 | 10/1995 |
| FR | 2745709 | 3/1996 |
| FR | 2730159 | 8/1996 |
| FR | 2800601 | 11/1999 |
| FR | 2801189 | 11/1999 |
| FR | 2808182 | 4/2000 |
| FR | 2874814 | 3/2006 |
| GB | 2157788 | 10/1985 |
| GB | 2173565 | 10/1986 |
| JP | 06-500039 | 6/1994 |
| JP | 06-319742 | 11/1994 |
| JP | 07-502419 | 3/1995 |
| JP | 07-184922 | 7/1995 |
| JP | 10-85232 | 4/1998 |
| JP | 11-89854 | 4/1999 |
| JP | 2003-010197 | 1/2003 |
| JP | 2003-126266 | 5/2003 |
| JP | 2003-526457 | 9/2003 |
| JP | 2006-516456 | 7/2006 |
| JP | 2007-54666 | 3/2007 |
| JP | 2011-509766 A | 3/2011 |
| JP | 2011-520580 | 7/2011 |
| JP | 4988203 | 7/2011 |
| JP | 5164571 | 8/2012 |
| JP | 64-52439 | 12/2012 |
| WO | WO 91/09572 | 12/1989 |
| WO | WO 93/04652 | 3/1993 |
| WO | WO 9404100 | 3/1994 |
| WO | WO 95/31158 | 11/1995 |
| WO | WO 96/28100 | 9/1996 |
| WO | WO 97/00054 | 1/1997 |
| WO | WO 99/52478 | 10/1999 |
| WO | WO 9953871 | 10/1999 |
| WO | WO 99/62417 | 12/1999 |
| WO | WO 00/12033 | 3/2000 |
| WO | WO 00/67652 | 5/2000 |
| WO | WO 00/53127 | 9/2000 |
| WO | WO 00/74605 | 12/2000 |
| WO | WO 00/76409 | 12/2000 |
| WO | WO 01/01895 | 1/2001 |
| WO | WO 0101893 | 1/2001 |
| WO | WO 01/12054 | 2/2001 |
| WO | WO 0117464 | 3/2001 |
| WO | WO 01/80751 | 11/2001 |
| WO | WO 02/43601 | 6/2002 |
| WO | WO 03/21308 | 3/2003 |
| WO | WO 03/43488 | 5/2003 |
| WO | WO 2004/008949 | 1/2004 |
| WO | WO 2004/064603 | 8/2004 |
| WO | WO 2004/078220 | 9/2004 |
| WO | WO 2004/078221 | 9/2004 |
| WO | WO 2004/098453 | 11/2004 |
| WO | WO 2005/112834 | 12/2005 |
| WO | WO 2005/112835 | 12/2005 |
| WO | WO 2006/017507 | 2/2006 |
| WO | WO 2006/047587 | 5/2006 |
| WO | WO 2006/058281 | 6/2006 |
| WO | wo 2006/063083 | 6/2006 |
| WO | WO 2006/065419 | 6/2006 |
| WO | WO 2006/081843 | 8/2006 |
| WO | wo 2006/108067 | 10/2006 |
| WO | WO 2007/028098 | 3/2007 |
| WO | WO 2007/048012 | 4/2007 |
| WO | wo 2007/119212 | 10/2007 |
| WO | WO 2007/124130 | 4/2008 |
| WO | WO 2008/044057 | 4/2008 |
| WO | WO 2008/064842 | 6/2008 |
| WO | WO 2008/070863 | 6/2008 |
| WO | WO 2007/009107 | 8/2008 |
| WO | WO 2009/092102 | 7/2009 |
| WO | WO 2009/064787 | 8/2009 |
| WO | WO 2009/124269 | 10/2009 |
| WO | WO 2009/143496 | 11/2009 |
| WO | WO 2009/147527 | 12/2009 |
| WO | WO 2009/152919 | 12/2009 |
| WO | WO 2010/068725 | 6/2010 |
| WO | WO 2010/136170 | 12/2010 |
| WO | WO 2010/148112 | 12/2010 |
| WO | WO 2011/079910 | 7/2011 |
| WO | WO 2011/142761 | 11/2011 |
| WO | WO 2011/150350 | 12/2011 |

(56) References Cited

FOREIGN PATENT DOCUMENTS

| | | |
|---|---|---|
| WO | WO 2012/009152 | 1/2012 |
| WO | WO 2012/089317 | 7/2012 |
| WO | WO 2012/135764 | 10/2012 |
| WO | WO 2013/006669 | 1/2013 |
| WO | WO 2013/023096 | 2/2013 |
| WO | WO 2013/025876 | 2/2013 |
| WO | WO 2013/043850 | 5/2013 |
| WO | WO 2013/082184 | 6/2013 |
| WO | WO 2013/158294 | 10/2013 |
| WO | WO 2013/173767 | 11/2013 |
| WO | WO 2013/184946 | 12/2013 |
| WO | WO 2014/018098 | 1/2014 |
| WO | WO 2014/026007 | 2/2014 |
| WO | WO 2014/035962 | 3/2014 |
| WO | WO 2014/088521 | 6/2014 |
| WO | WO 2014/116891 | 7/2014 |

OTHER PUBLICATIONS

International Patent Application No. PCT/US2013/029014, International Search Report dated Jul. 1, 2013, 7 pages.
Chiang, Biomechanical Comparison of Instrumented Posterior Lumbar Interbody Fusion with One or Two Cages by Finite Element Analysis, Spine, 2006, pp. E682-E689, vol. 31(19), Lippincott Williams & Wilkins, Inc.
Folman, Posterior Lumbar Interbody Fusion for Degenerative Disc Disease Using a Minimally Invasive B-Twin Expandable Spinal Spacer, Journal of Spinal Disorders & Techniques, 2003, pp. 455-460, vol. 16(5).
Gore, Technique of Cervical Interbody Fusion, Clinical Orthopaedics and Related Research, 1984, pp. 191-195, No. 188.
Hunt, Expanable cage placement via a posterolateral approach in lumbar spine reconstructions, Journal of Neurosurgery: Spine, 2006, pp. 271-274, vol. 5.
Krbec, [Replacement of the vertebral body with an expansion implant (Synex)], Acta Chir Orthop Traumatol Cech, 2002, pp. 158-162, vol. 69(3).
Polikeit, The importance of the endplate for interbody cages in the lumbar spine, Eur Spine J, 2003, pp. 556-561, vol. 12.
Shin, Posterior Lumbar Interbody Fusion via a Unilateral Approach, Yonsei Medical Journal, 2006, pp. 319-325, vol. 47(3).
Hoogland, T. et al., Total Lumbar Intervertebral Disc Replacement: testing of a New Articulating Space in Human Cadaver Spines—24 1 Annual ORS, Dallas TX, Feb. 21-23, 1978, 8 pages.
Spine Solutions Brochure—Prodisc 2001, 16 pages.
Link SB Charite Brochure—Intervertebral Prosthesis 1988, 29 pages.
Alfen et al., "Developments in the Area of Endoscopic Spine Surgery", European Musculoskeletal Review 2006, pp. 23-24.
ThessysTM, Transforaminal Endoscopic Spine Systems, joi max Medical Solutions.
Brooks, M.D. et al., "Efficacy of Supplemental Posterior Transfacet Pedicle Device Fixation in the Setting of One- or Two-Level Anterior Lumbar Interbody Fusion", retrieved Jun. 19, 2017, 6 pages.
Brochure for PERPOS PLS System Surgical Technique by Interventional Spine, 2008, 8 pages.
Paul D. Fuchs, "The use of an interspinous implant in conjunction with a graded facetectomy procedure", Spine vol. 30, No. 11, pp. 1266-1272, 2005.
Iprenburg et al., "Transforaminal Endoscopic Surgery in Lumbar Disc Herniation in an Economic Crisis—The TESSYS Method", US Musculoskeletal, 2008, pp. 47-49.
King, M.D., Don, "Internal Fixation for Lumbosacral Fusion", The Journal of Bone and Joint Surgery, J. Bone Joint Surg Am., 1948; 30: 560-578.
Morgenstern R; "Transforaminal Endoscopic Stenosis Surgery—A Comparative Study of Laser and Reamed Foraminoplasty", in European Musculoskeletal Review, Issue 1, 2009.
ProMap TM EMG Navigation Probe. Technical Brochure Spineology Inc., Dated May 2009.
Chin, Kingsley R., M.D. "Early Results of the Triage Medical Percutaneous Transfacet Pedicular BONE-LOK Compression Device for Lumbar Fusion", accessed online Jul. 10, 2017, 10 pages.
Niosi, Christina A., "Biomechanical Characterization of the three-dimentinoal kinematic behavior of the Dynesys dynamic stabilization system: an in vitro study", Eur Spine J. (2006) 15: pp. 913-922.
Manal Siddiqui, "The Positional Magnetic Resonance Imaging Changes in the Lumbar Spine Following Insertion of a Novel Interspinous Process Distraction Device", Spine vol. 30, No. 23, pp. 2677-2682, 2005.
Vikram Talwar, "Insertion loads of the X STOP Interspinous Process Distraction System Designed to Treat Neurogenic Intermittent Claudication", Eur Spine J. (2006) 15: pp. 908-912.
James F. Zucherman, "A Multicenter, Prospective, Randomized Trial Evaluating the X STOP Interspinous Process Decompression System for the Treatment of Neurogenic Intermittent Claudication", Spine, vol. 30, No. 12, pp. 1351-1358, 2005.
Kambin et al., "Percutaneous Lateral Discectomy of the Lumbar Spine: A Preliminary Report"; Clin. Orthop.; 1983; 174: 127-132.
Medco Forum, "Percutaneous Lumbar Fixation via PERPOS PLS System Interventional Spine", Sep. 2008, vol. 15, No. 37.
Medco Forum, "Percutaneous Lumbar Fixation via PERPOS System From Interventional Spine", Oct. 2007, vol. 14, No. 49.
Mahar et al., "Biomechanical Comparison of Novel Percutaneous Transfacet Device and a Traditional Posterior System for Single Level Fusion", Journal of Spinal Disorders & Techniques, Dec. 2006, vol. 19, No. 8, pp. 591-594.

* cited by examiner

FIG. 1A
FIG. 1B
FIG. 1C
FIG. 1D
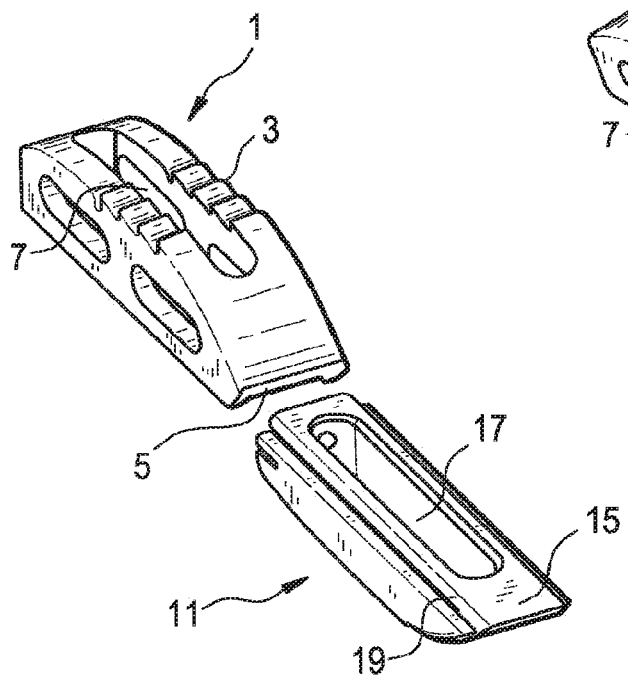
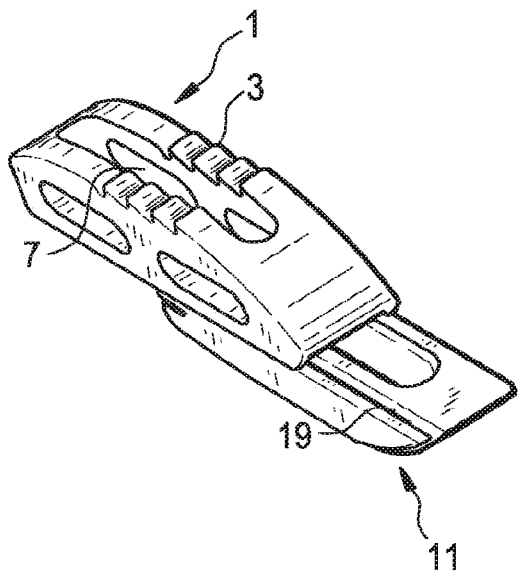
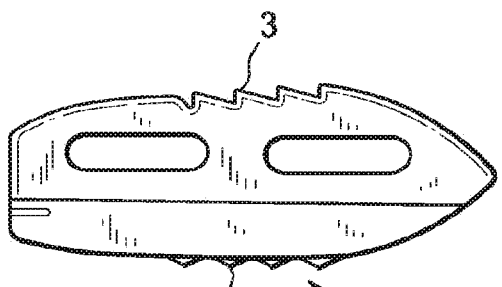
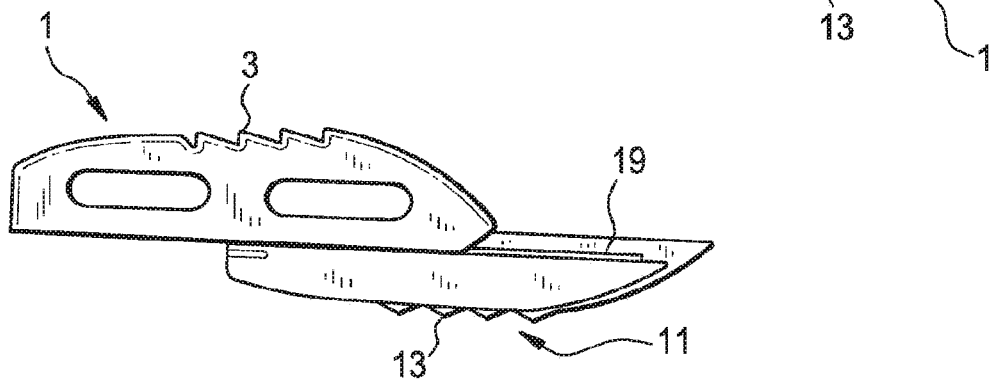

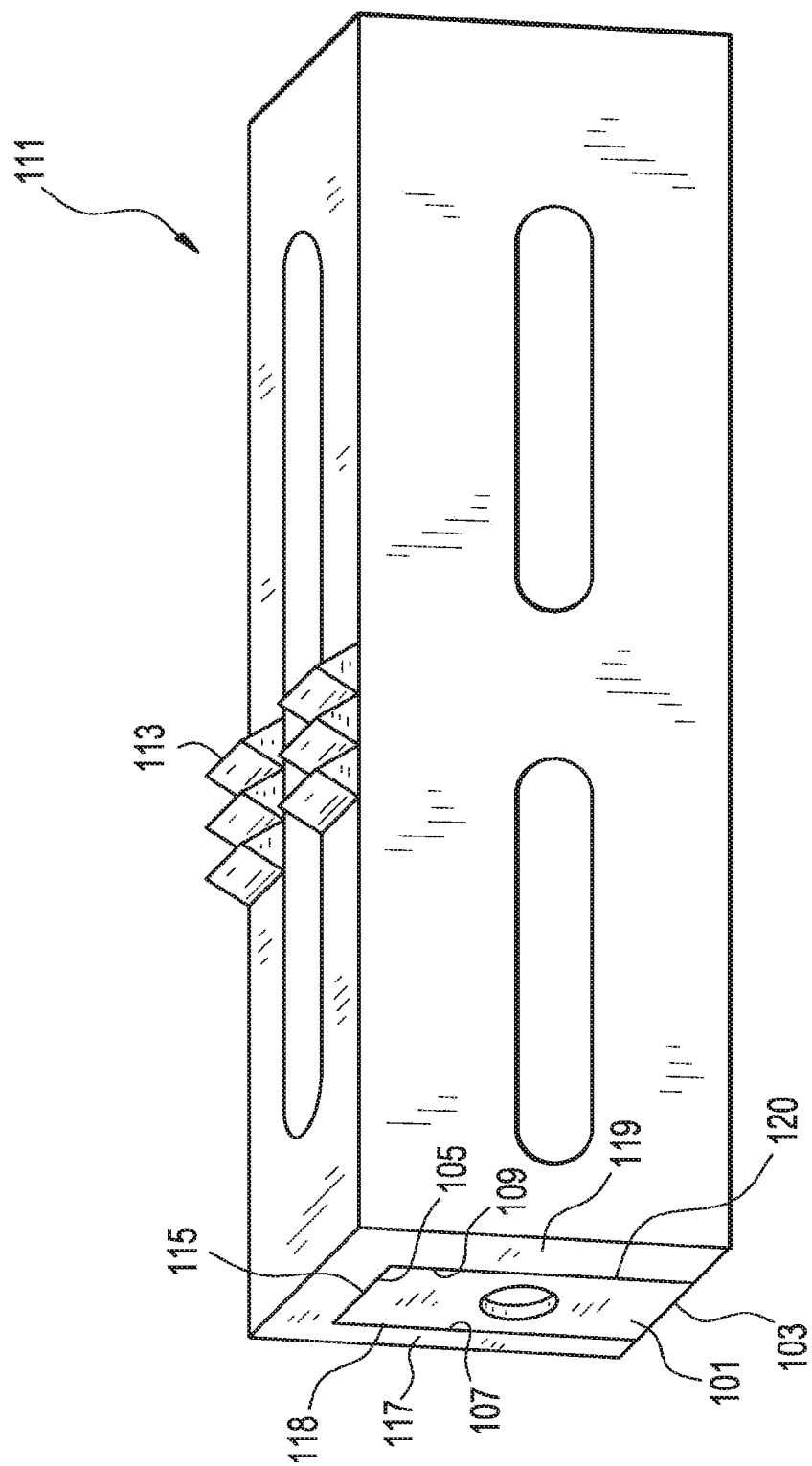

201

203

205

HIGHLY LORDOSED FUSION CAGE

CROSS-REFERENCE TO RELATED APPLICATIONS

This is a continuation application of U.S. patent application Ser. No. 14/514,700 filed Oct. 15, 2014, which in turn is a divisional application of U.S. patent application Ser. No. 11/768,636 filed Jun. 26, 2007, now issued as U.S. Pat. No. 8,900,307, the disclosures of both of which are hereby incorporated by reference as if set forth in their entirety herein.

BACKGROUND OF THE INVENTION

The natural intervertebral disc contains a jelly-like nucleus pulposus surrounded by a fibrous annulus fibrosus. Under an axial load, the nucleus pulposus compresses and radially transfers that load to the annulus fibrosus. The laminated nature of the annulus fibrosus provides it with a high tensile strength and so allows it to expand radially in response to this transferred load.

In a healthy intervertebral disc, cells within the nucleus pulposus produce an extracellular matrix (ECM) containing a high percentage of proteoglycans. These proteoglycans contain sulfated functional groups that retain water, thereby providing the nucleus pulposus within its cushioning qualities. These nucleus pulposus cells may also secrete small amounts of cytokines such as interleukin-1$\beta$ and TNF-$\alpha$ as well as matrix metalloproteinases ("MMPs"). These cytokines and MMPs help regulate the metabolism of the nucleus pulposus cells.

In some instances of disc degeneration disease (DDD), gradual degeneration of the intervetebral disc is caused by mechanical instabilities in other portions of the spine. In these instances, increased loads and pressures on the nucleus pulposus cause the cells within the disc (or invading macrophases) to emit larger than normal amounts of the above-mentioned cytokines In other instances of DDD, genetic factors or apoptosis can also cause the cells within the nucleus pulposus to emit toxic amounts of these cytokines and MMPs. In some instances, the pumping action of the disc may malfunction (due to, for example, a decrease in the proteoglycan concentration within the nucleus pulposus), thereby retarding the flow of nutrients into the disc as well as the flow of waste products out of the disc. This reduced capacity to eliminate waste may result in the accumulation of high levels of toxins that may cause nerve irritation and pain.

As DDD progresses, toxic levels of the cytokines and MMPs present in the nucleus pulposus begin to degrade the extracellular matrix, in particular, the MMPs (as mediated by the cytokines) begin cleaving the water-retaining portions of the proteoglycans, thereby reducing its water-retaining capabilities. This degradation leads to a less flexible nucleus pulposus, and so changes the loading pattern within the disc, thereby possibly causing delamination of the annulus fibrosus. These changes cause more mechanical instability, thereby causing the cells to emit even more cytokines, thereby upregulating MMPs. As this destructive cascade continues and DDD further progresses, the disc begins to bulge ("a herniated disc"), and then ultimately ruptures, causing the nucleus pulposus to contact the spinal cord and produce pain.

One proposed method of managing these problems is to remove the problematic disc and replace it with a porous device that restores disc height and allows for bone growth therethrough for the fusion of the adjacent vertebrae. These devices are commonly called "fusion devices".

U.S. Pat. No. 5,865,848 ("Baker") discloses a two piece intervertebral fusion cage having a ramp. Baker describes a intervertebral spacer comprised of two components. The two portions have opposed flanges connected by a screw to effect translation, and complimentary slopes. The components are inserted together in a collapsed condition. Post-insertion translation of one component relative to the other creates an expanded condition and the desired distraction. US Published Patent Application 2004/0230309 ("DePuy Spine") discloses a two piece intervertebral fusion cage having a ramp. See FIG. 14D.

US Published Patent Application Nos. US2003/0135275 and 2003/0139812 (collectively, "Garcia") disclose a two-piece implant formed by upper and lower halves, wherein the inner surfaces of the two halves form a dovetail joint that runs along a transverse axis of the implant.

SUMMARY OF THE INVENTION

The present invention is directed to a two-piece intervertebral fusion cage, comprising:
 a) an upper component having a first outside surface adapted for gripping an upper vertebral endplate and a first interior surface,
 b) a lower component having a second outside surface adapted for gripping a lower vertebral endplate and a second interior surface, wherein the interior surfaces mate.

One advantage of such a cage is its easy insertion. In a first step, the lower component is inserted into the disc space and is held in place. The first step confirms placement of the implant and its footprint. In a second step, the upper component is inserted into the disc space by sliding its interior surface along the opposed interior surface of the lower component. This two-step method of insertion eliminates the need to provide an independent distraction means, such as the use of an impaction hammer, and an independent trialing means. It also provides mechanical leverage in the cage to facilitate the creation of lordosis.

A second advantage of such a cage is its impact on patient safety. The gradual nature of the distraction of the disc space provided by this two-step insertion procedure should also reduce the possibility of over-distraction, which can cause neural damage. It also eliminates hammer-induced sudden impaction during cage insertion, thereby reducing cage failures, over-insertion and anterior damage. Lastly, the smaller height of the annular defect produced during device insertion aids in preventing device expulsion.

In a first aspect of the present invention, the outside surface of at least one of the components is substantially parallel to its corresponding interior surface. This provides the advantage of ease of insertion through a small annular defect/incision. Simply, one component can determine height and the other component can determine lordosis.

In a second aspect of the present invention, each component has a throughhole extending from its outside surface to its interior surface, and the interior surfaces of these components mate to align the first and second throughholes. This alignment provides a path for bone growth through the vertical dimension of the device, thereby facilitating fusion between the vertebral endplates.

In a third aspect of the present invention, each component has opposed sidewalls and at least one of the components has a lateral throughhole extending from a sidewall thereof to its opposed sidewall. This lateral throughhole provides a path for increased vascularization, increased diffusion, and bone growth through the lateral dimension of the device, thereby facilitating fusion between the vertebral endplates.

In a fourth aspect of the present invention, each component has a dovetail feature extending along the longitudinal axis of its interior surface and the dovetail features of the corresponding components mate along the longitudinal axes. This mating of dovetails provides for a locking of the mated upper and lower components and increases the assurance that the mated components will not disengage in vivo.

In a fifth aspect of the present invention, the upper component has a tapered distal end, preferably a bulleted nose. This tapered distal end allows for easy distraction of the opposed vertebral endplates upon insertion of the upper component into the disc space.

DESCRIPTION OF THE FIGURES

FIGS. 1a, 1b, 1c, and 1d disclose a cage of the present invention having mating dovetail features and aligned vertical throughholes.

FIGS. 5b and 5c disclose a method of inserting the device of FIG. 5a.

FIG. 6 discloses a cage of the present invention wherein one of the components has extending side walls that create a housing adapted to capture the other component.

DETAILED DESCRIPTION OF THE FIGURES

For the purposes of the present invention, the terms "inner surface", "inside surface" "interior surface are interchangeable, as are the terms "exterior surface", "outer surface" and "outside surface".

Figure 1E:
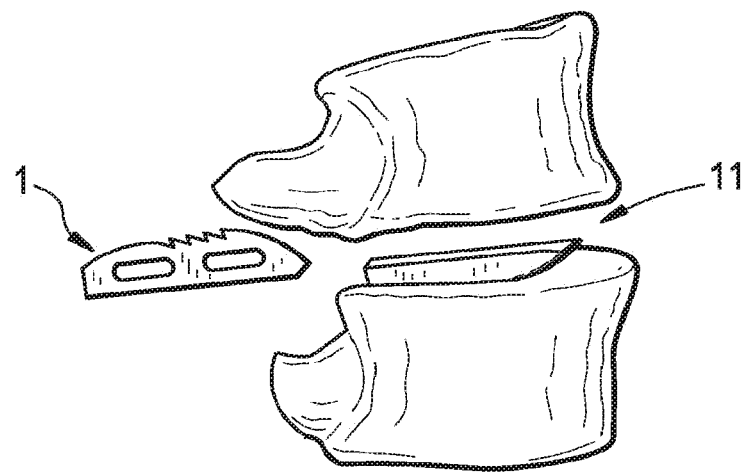
FIGS. 1e, 1f, and 1g disclose the sequential insertion and assembly of the components of the device into the disc space.
Figure 1F:
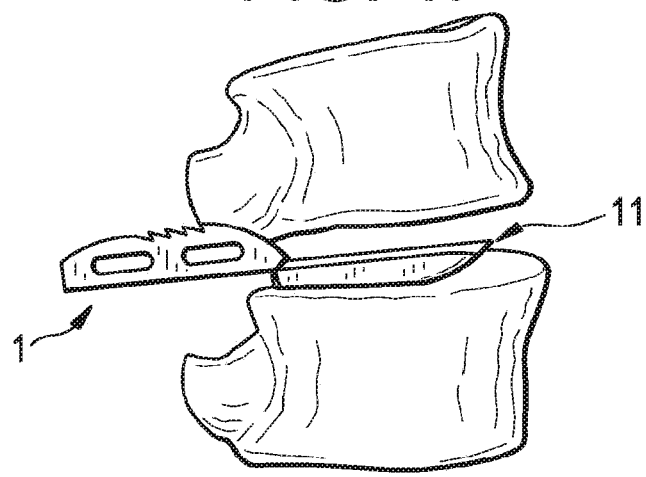
Figure 1G:
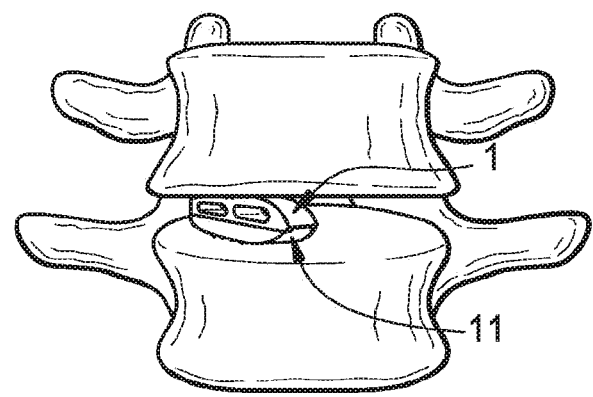

In general, the cage possesses a two-piece structure with hard-endplates and a locking means that is compatible with MIS techniques. Both the top and bottom portions have an interior and exterior surface (FIG. 1), where the exterior surface interfaces with the vertebra.

Now referring to FIGS. 1a-1d, there is provided an intervertebral fusion cage, comprising:
a) an upper component 1 having a first outside surface 3 adapted for gripping an upper vertebral endplate, a first interior surface 5 having a first longitudinal axis, a first throughhole 7 extending from the outside surface to the first interior surface, and a first dovetail feature (not shown) extending along the first longitudinal axis, and
b) a lower component 11 having a second outside surface 13 adapted for gripping a lower vertebral endplate, a second interior surface 15 having a second longitudinal axis, a second throughhole 17 extending from the outside surface to the second interior surface, and a second dovetail feature 19 extending along the first longitudinal axis, wherein the interior surfaces mate to align the first and second throughholes.

The device of FIGS. 1a-1d possesses mating dovetail features on its interior surfaces. These features help maintain the device in its assembled form. The device of FIGS. 1a-1d also possesses aligned vertical throughholes through each component in its assembled form. These aligned holes help provide desirable bone growth through the device.

In use, the component halves of the device of the present invention are inserted into the disc space is a sequential fashion and are assembled in situ. Now referring to FIG. 1e, the lower component 11 is first inserted into the disc space, with the tapered portion pointing posteriorly, so that it rests upon the floor of the disc space. The reduced height of the lower component allows it to be inserted without any need for distraction. Now referring to FIG. 1f, the inside surface of the upper component is mated to the inside surface of the lower component and advanced into the disc space. Because the height of the combined components is greater than the disc space, and because the nose of the upper component is tapered, gradual insertion of the upper component into the disc space in this manner provides a gradual distraction of the disc space. Now referring to FIG. 1g, the assembled component is located within the disc space.

In one embodiment, the interior surface of the top and/or bottom portion is generally parallel to their exterior surface. Now referring to FIG. 2, there is provided an intervertebral fusion cage, comprising:
a) an upper component 21 having a first outside surface 23 adapted for gripping an upper vertebral endplate and a first interior surface 25, a first sidewall 27 and a second opposed sidewall (not shown),
b) a lower component 31 having a second outside surface 33 adapted for gripping a lower vertebral endplate and a second interior surface 35, a third sidewall 37 and a second fourth sidewall (not shown), wherein the interior surfaces mate, wherein at least one of the components has a lateral throughhole 39 extending from a sidewall thereof to its opposed sidewall, and wherein at least one of the outside surfaces is substantially parallel to its corresponding interior surface.

An alternative embodiment would have sloped sides and/or non-parallel throughhole walls. These walls may be curved inwards (concave) or bowed outward (convex). Such an embodiment would increase the mechanical structural stability of the assembled device. Additionally, increasing the devices' mating surface areas would give additional room for the dovetail and locking features. Simultaneously, increased mating surface areas would decrease normal and shear load distributions at the mating surfaces, thereby decreasing likelihood of mechanical failures and further minimizing potential for the generation of particulate wear debris.

Figure 2:
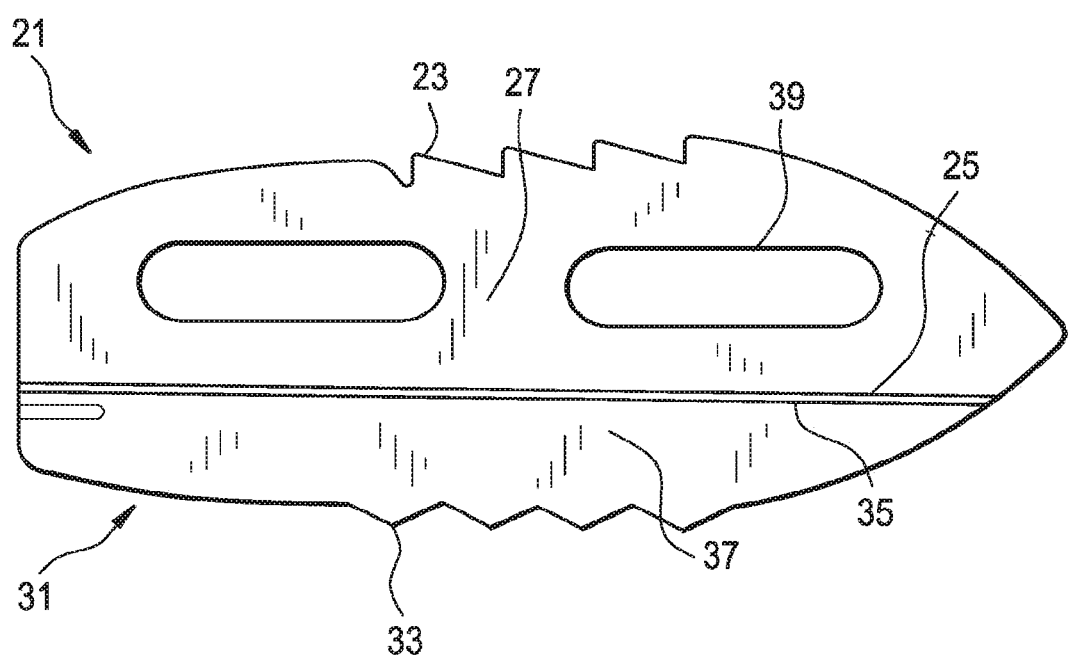
FIG. 2 discloses a cage of the present invention having a lateral throughhole extending from a sidewall thereof to its opposed sidewall, and an outside surfaces that is substantially parallel to its corresponding interior surface.

The device of FIG. 2 possesses a component that has parallel outside and interior surface. The device of FIG. 2 also possesses aligned lateral throughholes through at least one of its components. These holes help in desirable bone growth through the device.

Figure 3:
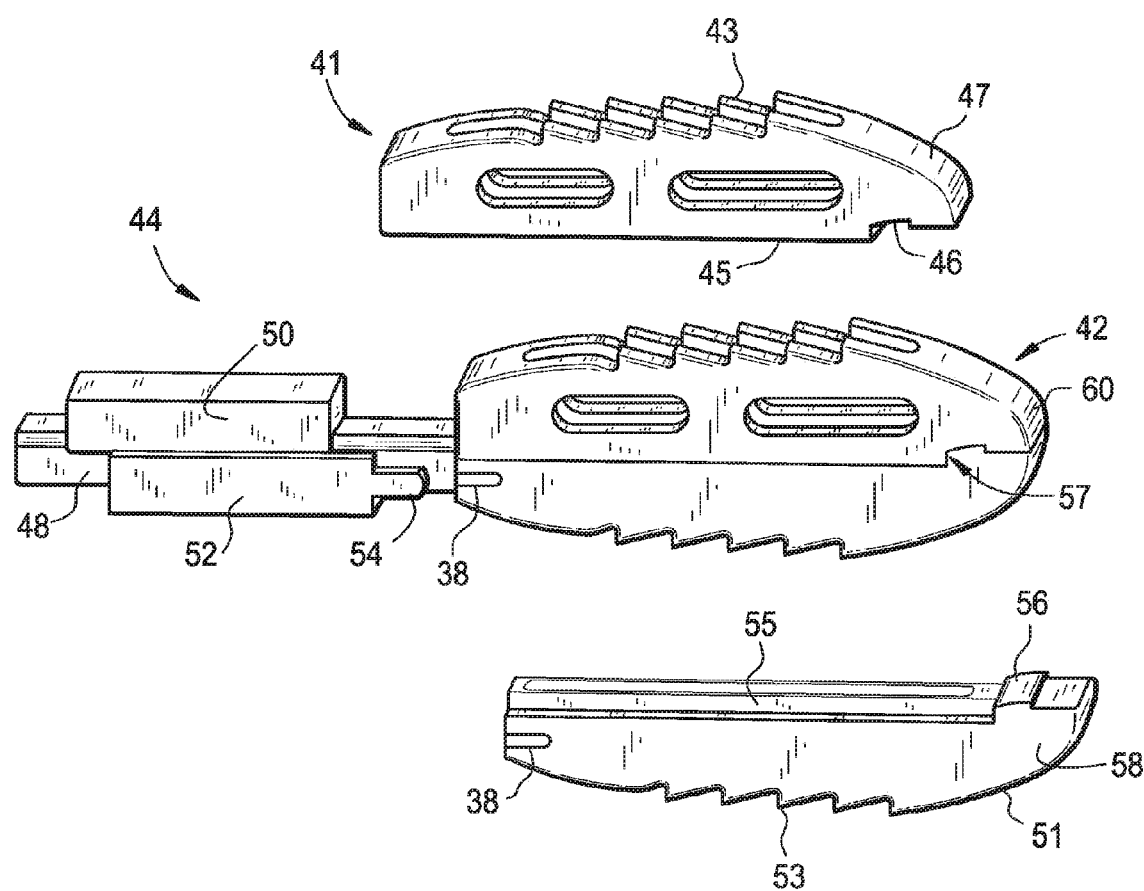
FIG. 3 discloses an exploded cage of the present invention having a bulleted distal nose, along with an assembled cage attached to an insertion instrument.

Now referring to FIG. 3, there is provided the upper 41 and lower 51 halves of the intervertebral fusion cage of the present invention, along with an assembled cage 42 attached to an insertion instrument 44. The intervertebral fusion cage comprises:
 a) an upper component 41 having a first outside surface 43 adapted for gripping an upper vertebral endplate, a first interior surface 45 having a recess 46, and a tapered distal end 47,
 b) a lower component 51 having a second outside surface 53 adapted for gripping a lower vertebral endplate and a second interior surface 55 having a projection 56 and a taper distal end 58, wherein the interior surfaces mate so that the recess and projection form a stop 57 and the tapered distal ends form a bullet nose 60.

The upper component of the device of FIG. 3 possesses a bullet distal nose. This bullet nose helps the upper component distract the disc space as it is inserted into the disc space. The insertion instrument 44 includes a rail 48, a top pusher 50, and a bottom rod 52 having a projection 54 that mates with a recess 38 in the lower component of the cage.

Figure 4:
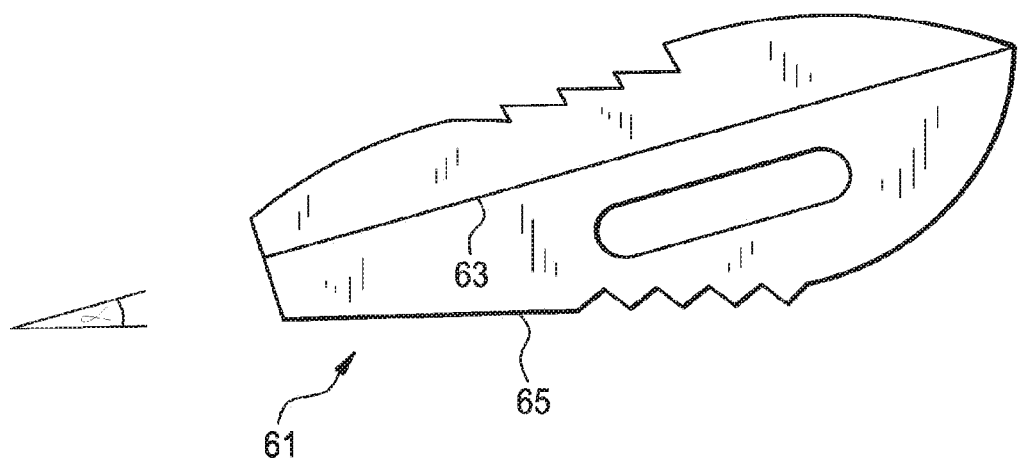
FIG. 4 discloses an interior surface of the lower component that is angled with respect to its corresponding outer surface, thus creating lordosis.

In another embodiment, the interior surface 63 of the lower component 61 creates a ramp having an angle a with respect to its corresponding outer surface 65 (FIG. 4). The upper component 67 of the implant translates along this ramp, creating lordosis.

Because the two pieces of the cage are inserted sequentially into the disc space, the "insertion" height of the assembly and thus the height of the annular defect required during the insertion is approximately one half of the assembled device height.

Figure 5A:
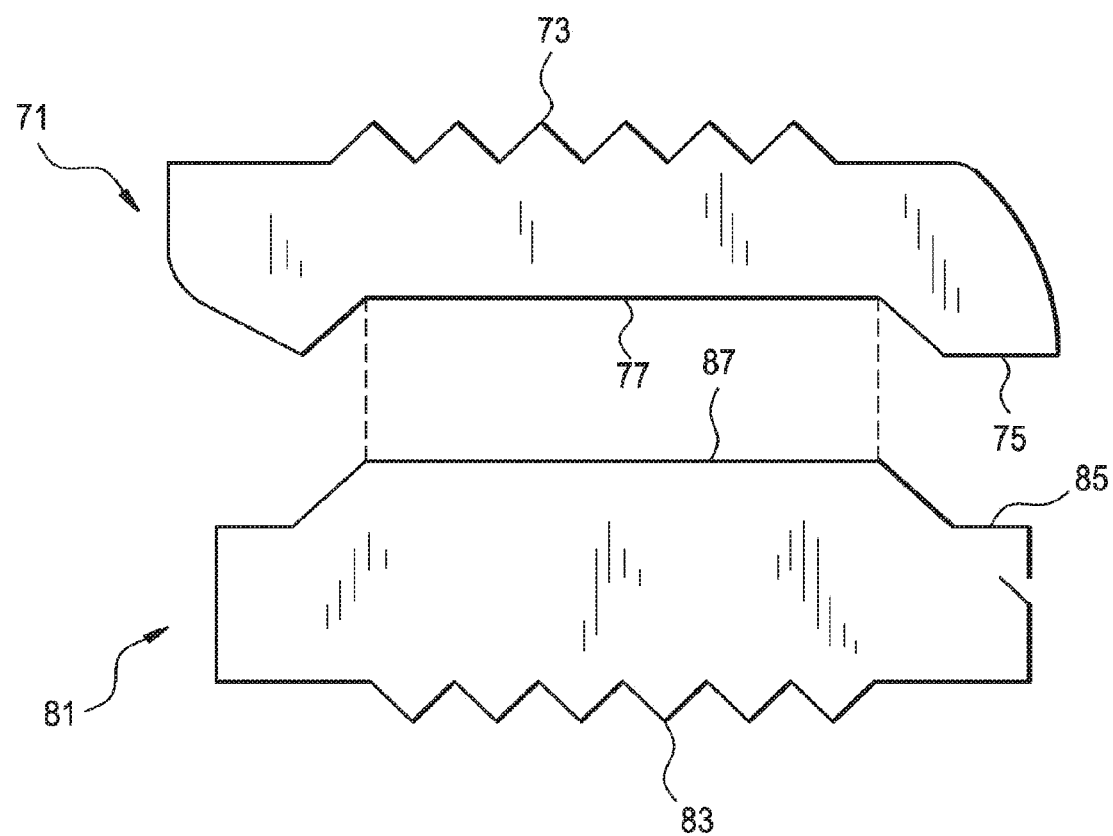
FIG. 5a discloses a cage of the present invention wherein an inside surface of the first component has a recess, and an inside surface of the second component has an extension, wherein the recess and extension mate to provide nesting of the components.

Now referring to FIG. 5a, there is provided an intervertebral fusion cage, comprising:
 a) a first component 71 having a first outside surface 73 adapted for gripping a first vertebral endplate, a first interior surface 75, and a recess 77 in the first interior surface extending toward the first outside surface,
 b) a second component 81 having a second outside surface 83 adapted for gripping a second vertebral endplate, a second interior surface 85, and an extension 87 extending from the second interior surface toward the first interior surface, wherein the recess and extension of the interior surfaces mate to provide nesting of the components.

Figure 5B:
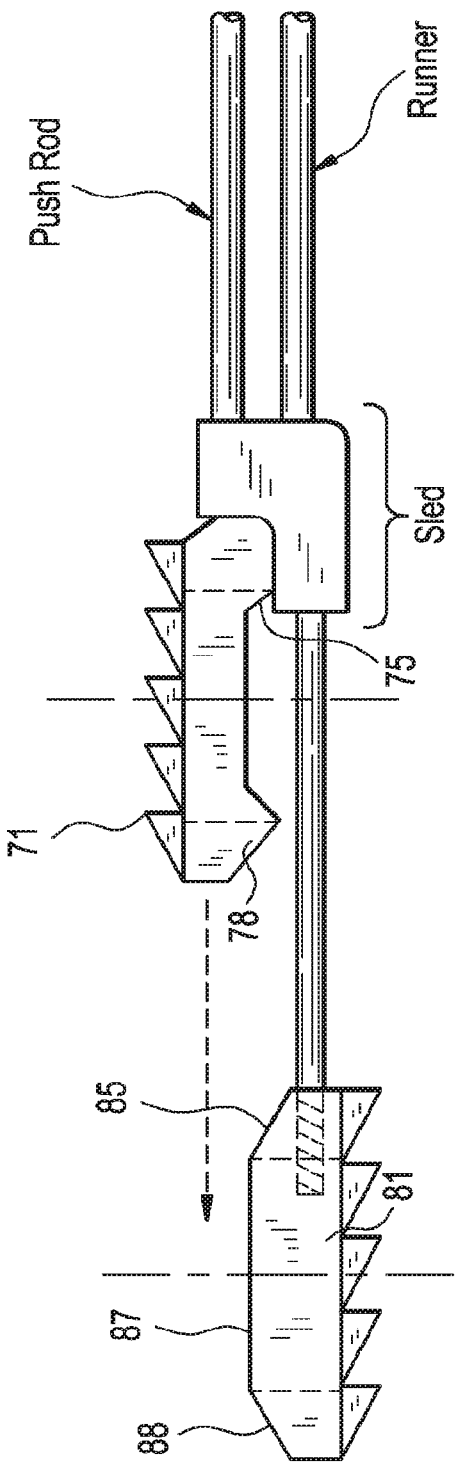
Figure 5C:
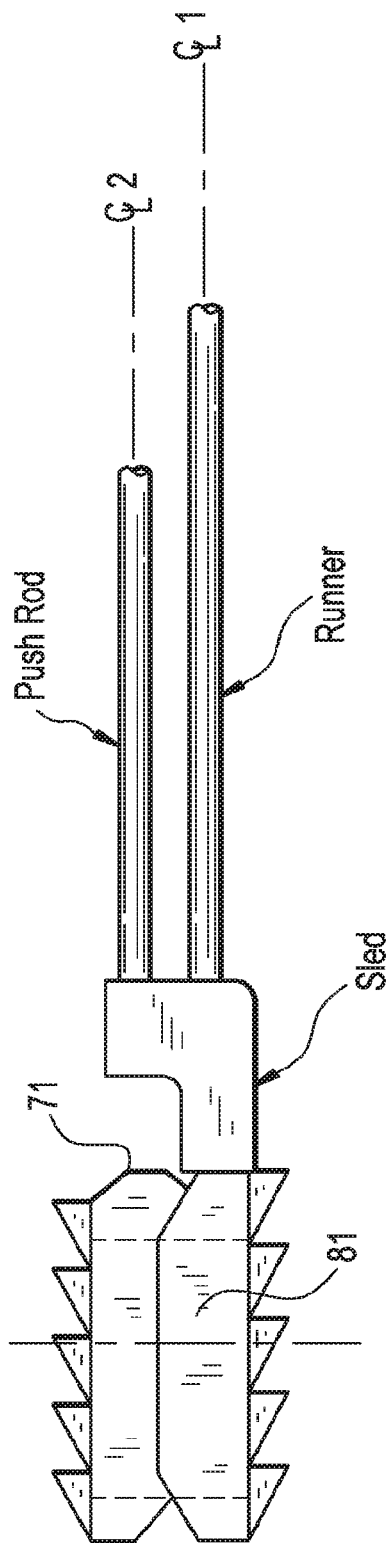

Now referring to FIGS. 5b and 5c, there is provided a method of inserting the nested cage of FIG. 5a: Place the baseplate 81 in the interbody disc space. Position and slide the overrider plate 71 onto and over the baseplate 81. Initially, the overrider nose 78 will slide across the base plate's interior surface 87 thereby creating a slight over-distraction of the disc space. As the overrider's posterior aspect 75 approaches the baseplate's posterior niche 85, the anterior overrider nose 78 will fall into the anterior niche 88 thereby providing a positive stop and locking mechanism to seat the overrider plate 71 onto the baseplate 81.

The preferred method for the order of insertion of the two-piece cage of the present invention is now disclosed. The first step can be placement of the first component of the device against the inferior vertebral body. This is often followed by insertion and eventual assembly of the second component onto and over the first component. The first component should contain a lordosed or angled component such that the surface over which the second component is inserted is substantially parallel to the superior vertebral endplate.

Alternatively, the method of inserting the first component with substantially parallel bone contacting and interior surfaces requires that the second component to contain a lordotic angle. As this two-piece assembled cage is typically inserted from a posterior approach, and the angle of the interbody cavity widens anteriorly, insertion of the second component with a lordotic angle requires over-distraction of the posterior aspect of the interbody space to accommodate the larger/taller anterior aspect of the second component. This over-distraction and the associated increased insertion force is not associated with the preferred method where the lordosed component is inserted first followed by the height-restoring component with substantially parallel sides.

Now referring to FIG. 6, there is provided an intervertebral fusion cage, comprising:
 a) a first component 101 having a first outside surface 103 adapted for gripping an upper vertebral endplate and a first interior surface 105, a first sidewall 107 extending between the first outside surface and the first interior surface and having an outer surface (not shown) and a second opposed sidewall 109 extending between the first outside surface and the first interior surface and having an outer surface (not shown),
 b) a housing component 111 having a second outside surface 113 adapted for gripping a lower vertebral endplate and a second interior surface 115, a third sidewall 117 extending from the second interior surface and away from the second outside surface and having an inner surface 118, and a fourth sidewall 119 extending from the second interior surface and away from the second outside surface and having an inner surface 120, wherein the interior surfaces mate, and wherein the outer surfaces of the first component mates with their respective inner surfaces of the housing component.

In FIG. 6, one of the components has extending side walls that create a housing adapted to capture the other component. The advantage of this embodiment is that it possesses an enhanced dovetail creating enhanced stability.

Figure 7A:
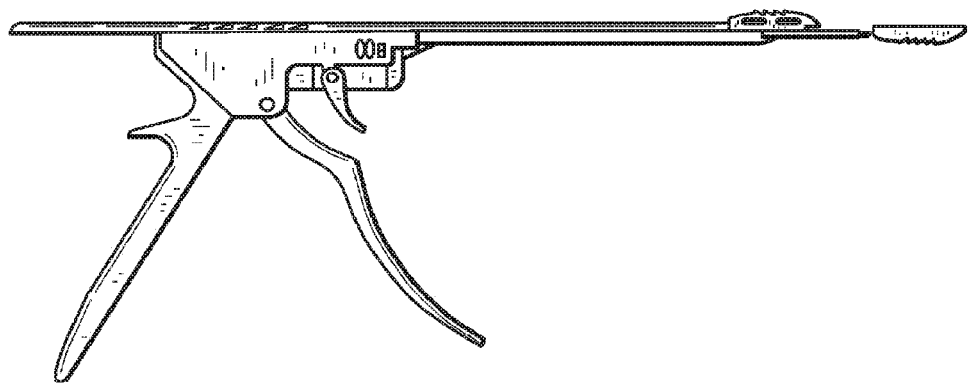
FIGS. 7a and 7b disclose the device of the present invention attached to an insertion instrument.
Figure 7B:
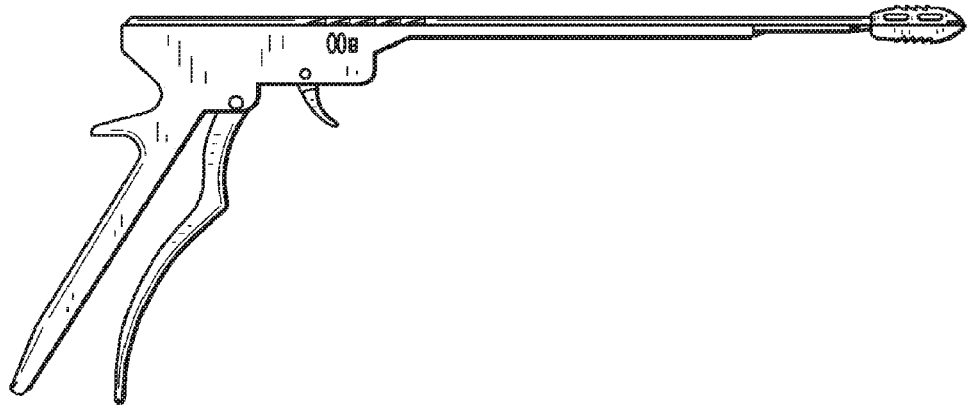

Now referring to FIGS. 7a-b, there is provided a device for inserting the components of the present invention into the disc space. FIG. 7a discloses the disposition of the instrument during insertion of the inferior component into the disc space. FIG. 7b discloses the disposition of the device when the upper component is advanced into the disc space to the point where it rides on top of the lower component and forms the assembly.

The endplates may have teeth to prevent migration and perforations to allow bone growth.

Radiographic markers can be incorporated to allow intra- or post-operative visualization.

Additionally, the outside surfaces of the superior and inferior portions can be designed with varying geometries to allow for their customization to the patient's anatomy, thereby minimizing the risk of subsidence. For instance, the outside surface of the superior half may have a convex dome while the outside surfaces of the inferior half may be flat, convex, concave or serpentine (concave posterior and convex anterior).

Figure 8A:
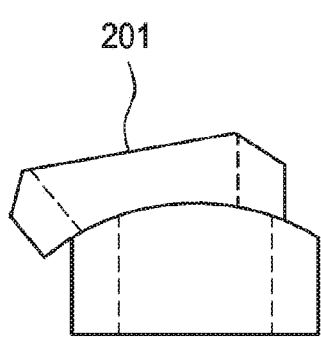
FIGS. 8a. 8b, and 8c disclose arcuate cages of the present invention.
Figure 8B:
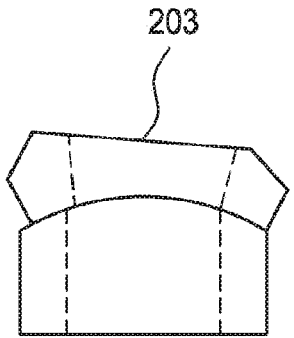
FIG. 8d discloses an arcuate cage inserted into a disc space.
Figure 8C:
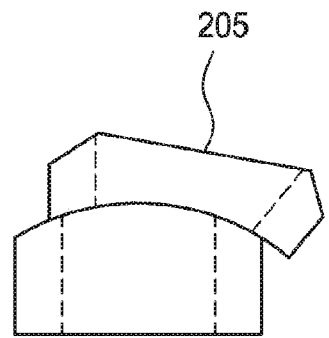
Figure 8D:
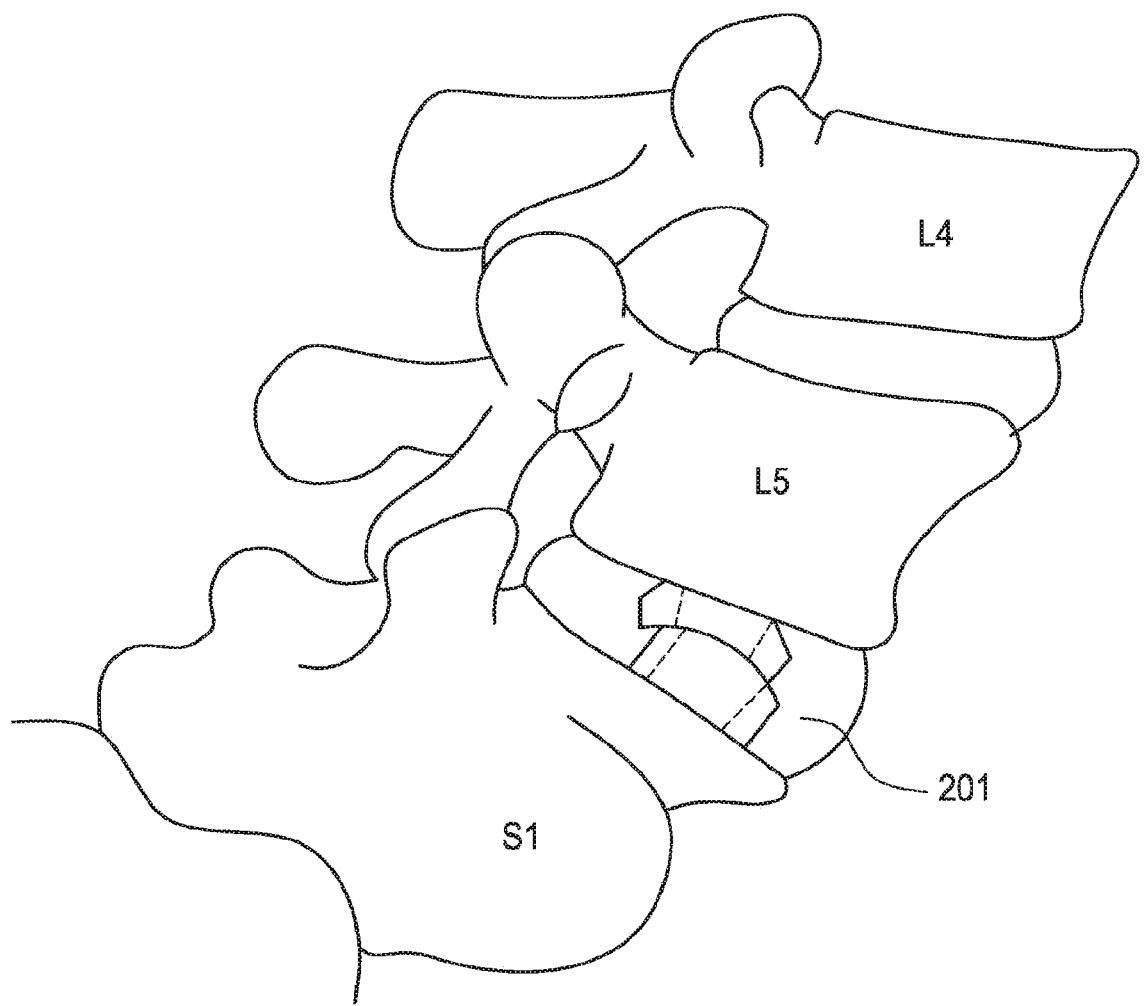

In an alternative embodiment, an arcuate sliding mating pathway is contemplated. FIGS. 8a-8c disclose arcuate cages of the present invention forming a lordotic angle 201 (FIG. 8a), no angle 203 (FIG. 8b) and a kyphotic angle 205 (FIG. 8c). FIG. 8d discloses a lordotic arcuate cage 201 inserted into a disc space.

The benefit to assembling the two cage halves using an arcuate assembly pathway is the potential to provide in situ determination of lordotic angle. Also, the arcuate pathway would embody a mechanism allowing a continuously variable lordotic angle (as opposed to discrete lordotic angles represented by assembly of different superior or inferior cage components). The arcuate mating mechanism requires that one half of the cage contains a convex mating surface while the other half contains a concave mating surface with an arcuate geometry that exactly mimics the inverse of the opposite curve. The assembled halves would represent a fixed radial distance about some center of rotation (the geometric centroid of the arcuate pathway). This fixed radial distance represents the cage height. As the superior cage half slides along the arcuate mating surface of the inferior cage half, the lordotic angle of the assembly will vary continuously. Detents, stops, or teeth can be inserted into the arcuate pathway to create discrete increments of lordotic angles along the continuous arcuate pathway, if this is a preferred further embodiment.

The arcuate pathway enables similar seating features compared to the planar device mating pathway—dovetails, keyways, detents, snap-fits, set screws, etc.

The two halves of the device may be secured together by various means. For instance, a dovetail feature may be incorporated into the interior surfaces of the top and bottom portions for ease of insertion, as shown in FIGS. 1a-f, 2 and 3. The two components may also be stacked and nested together without a dovetail, as shown in FIGS. 5a-c, or the superior/inferior half may have side walls creating a housing that captures the other portion, as shown in FIG. 6. The two portions of the device may be locked together in a variety of locking means including but not limited to Morse taper locks, positive stop(s), ultrasonic welding, snap mechanism (s), a set screw, a clip, a collet, cams, etc. Additional design features can be included to aid in seating the two halves: mechanical keys, a threaded nut can screw onto threaded features on the posterior aspect of each half, and a mechanical channel can be incorporated into the design for the use of curing compounds like adhesives and grouts.

Both components of the device may also incorporate a variety of holding means to assist during the insertion of the device. These holding means may be located on the interior or exterior surfaces as well as along the sidewalls. For example, the top and/or bottom portion may have threaded holes, divots, or slots to provide for secure holding and cage support during insertion, placement and assembly.

After placing the inferior portion, the superior portion can be inserted by several means to expand the overall device height and provide appropriate lordosis or kyphosis.

The superior and inferior portions are generally hollow to provide for filling with various osteogenic fillers and can be porous to allow for graft filling, bony ingrowth and spinal fusion. Lateral openings can also be incorporated to increase vascularization of the osteogenic fillers as well as to provide post-operative visualization of the bony fusion process. Filling can be done preoperatively or intraoperatively, as a through hole into the wedge can facilitate filling of the entire construct in situ.

Unlike traditional single-piece cages, the two-piece assembled cage requires sliding articulation of two half-cages packed with bone. Bone packed within a cage is typically held in place using friction forces. The sliding assembly mechanisms described could potentially dislodge packed bone graft during cage insertion and/or assembly. To mitigate the dislodgement of bone chips or the potential for sliding-interference of the bone chips, bonding a resorbable lamina of material between the two halfs is proposed. Such a lamina could be placed on the interior surface 45 of the upper half 43 (see FIG. 3). Such a resorbable member could be applied to all cage openings but is of particular utility to prevent dislodgement or interference of the bone graft during sliding assembly of the two halves.

The present invention also offers novel trialing methods. The inferior or superior portion of the implant device can be inserted alone to confirm disc space clearance and device placement, and a trial of the superior component can be placed upon the inserted component to confirm disc height, lordosis, and placement.

Because these cages reduce the profile required for their insertion, they allow for implantation through a cannula that may be smaller than the conventional cannula.

The endplates can be made of any structural biocompatible material including resorbable (PLA, PLGA, etc.), non-resorbable polymers (CFRP, PEEK, UHMWPE, PDS), metallics (SS, Ti-6Al-4V, CoCr, etc.), as well as materials that are designed to encourage bony regeneration (allograft, bone substitute-loaded polymers, growth factor-loaded polymers, ceramics, etc.). The materials for the upper and lower components are biocompatible and generally similar to those disclosed in the prior art. Examples of such materials are metal, PEEK and ceramic.

In preferred embodiments, each of the upper and lower components is manufactured from a material that possesses the desirable strength and stiffness characteristics for use as a fusion cage component.

These components of the present invention may be made from any non-resorbable material appropriate for human surgical implantation, including but not limited to, surgically appropriate metals, and non-metallic materials, such as carbon fiber composites, polymers and ceramics.

In some embodiments, the cage material is selected from the group consisting of PEEK, ceramic and metallic. The cage material is preferably selected from the group consisting of metal and composite (such as PEEK/carbon fiber).

If a metal is chosen as the material of construction for a component, then the metal is preferably selected from the group consisting of titanium, titanium alloys (such as Ti-6Al-4V), chrome alloys (such as CrCo or Cr—Co—Mo) and stainless steel.

If a polymer is chosen as a material of construction for a component, then the polymer is preferably selected from the group consisting of polyesters, (particularly aromatic esters such as polyalkylene terephthalates, polyamides; polyalkenes; poly(vinyl fluoride); PTFE; polyarylethyl ketone PAEK; polyphenylene and mixtures thereof.

If a ceramic is chosen as the material of construction for a component, then the ceramic is preferably selected from the group consisting of alumina, zirconia and mixtures thereof. It is preferred to select an alumina-zirconia ceramic, such as BIOLOX Delta™, available from CeramTec of Plochingen, Germany. Depending on the material chosen, a smooth surface coating may be provided thereon to improve performance and reduce particulate wear debris.

In some embodiments, the cage member comprises PEEK. In others, it is a ceramic.

In some embodiments, the first component consists essentially of a metallic material, preferably a titanium alloy or a chrome-cobalt alloy. In some embodiments, the second component consists essentially of the same metallic material as the first plate.

In some embodiments, the components are made of a stainless steel alloy, preferably BioDur® CCM Plus® Alloy available from Carpenter Specialty Alloys, Carpenter Technology Corporation of Wyomissing, Pa. In some embodiments, the outer surfaces of the components are coated with a sintered beadcoating, preferably Porocoat™, available from DePuy Orthopaedics of Warsaw, Ind.

In some embodiments, the components are made from a composite comprising carbon fiber. Composites comprising carbon fiber are advantageous in that they typically have a strength and stiffness that is superior to neat polymer materials such as a polyarylethyl ketone PAEK. In some embodiments, each component is made from a polymer composite such as a PEKK-carbon fiber composite.

Preferably, the composite comprising carbon fiber further comprises a polymer. Preferably, the polymer is a polyarylethyl ketone (PAEK). More preferably, the PAEK is selected from the group consisting of polyetherether ketone (PEEK), polyether ketone ketone (PEKK) and polyether ketone (PEK). In preferred embodiments, the PAEK is PEEK.

In some embodiments, the carbon fiber comprises between 1 vol % and 60 vol % (more preferably, between 10 vol % and 50 vol %) of the composite. In some embodiments, the polymer and carbon fibers are homogeneously mixed. In others, the material is a laminate. In some embodiments, the carbon fiber is present in a chopped state. Preferably, the chopped carbon fibers have a median length of between 1 mm and 12 mm, more preferably between 4.5 mm and 7.5 mm. In some embodiments, the carbon fiber is present as continuous strands.

In especially preferred embodiments, the composite comprises:
  a) 40-99% (more preferably, 60-80 vol %) polyarylethyl ketone (PAEK), and
  b) 1-60% (more preferably, 20-40 vol %) carbon fiber, wherein the polyarylethyl ketone (PAEK) is selected from the group consisting of polyetherether ketone (PEEK), polyether ketone ketone (PEKK) and polyether ketone (PEK).

In some embodiments, the composite consists essentially of PAEK and carbon fiber. More preferably, the composite comprises 60-80 wt % PAEK and 20-40 wt % carbon fiber. Still more preferably the composite comprises 65-75 wt % PAEK and 25-35 wt % carbon fiber.

Although the present invention has been described with reference to its preferred embodiments, those skillful in the art will recognize changes that may be made in form and structure which do not depart from the spirit of the invention.

Alternatively, combinations of cage materials could be beneficial (i.e.,—a ceramic bottom half with a PEEK top half).

What is claimed:

1. An implant configured to be implanted into an intervertebral space between first and second vertebrae, the implant comprising:
  a first component having:
    proximal and distal ends that are spaced from one another along a first direction;
    first and second sides that are spaced from one another along a second direction, perpendicular to the first direction; and
    a first inner surface and a first outer surface that are spaced from one another along a third direction, perpendicular to both the first and second direction, the first outer surface configured to grip one of the first and second vertebrae, wherein the first component defines a through hole that extends from the first outer surface to the first inner surface along the third direction, and the first component further defines a recess that extends into the first inner surface with respect to the third direction and terminates between the first inner surface and first outer surface, the recess further extending through the first and second sides along the second direction; and
  a second component having a pair of sides that are spaced from one another along the second direction, and having a second inner surface configured to face the first component along the third direction, the second component having a projection that extends between the sides of the pair of sides along the second direction such that the projection has a maximum length along the second direction, a maximum height along the third direction, and a maximum width along the first direction, the maximum length being greater than the maximum height and the maximum width, and the projection being configured to mate with the recess when the second component is coupled to the first component.

2. The implant of claim 1, wherein the first direction is aligned with an insertion direction of the implant, and the first and second inner surfaces extend parallel to the insertion direction.

3. The implant of claim 1, wherein the second component defines a through hole that extends through second inner surface along the third direction.

4. The implant of claim 3, wherein the through hole of the second component is aligned with the through hole of the first component along the third direction.

5. The implant of claim 1, wherein the projection limits movement of the first component along the first direction.

6. The implant of claim 1, wherein the projection includes a ramped surface that faces in a direction that extends towards the first outer surface of the first component when the second component is coupled to the first component.

7. The implant of claim 1, wherein the projection includes a ramped surface that ramps in a direction that extends towards the first outer surface of the first component, when the second component is coupled to the first component, as the ramped surface extends along an insertion direction that extends from the trailing end towards the insertion end.

8. The implant of claim 1, wherein the second component includes proximal and distal ends that are spaced from one another along the first direction, and the distal end of the second component is tapered.

9. The implant of claim 1, wherein the recess is defined by a first internal surface and a second internal surface that are spaced from one another along the first direction.

10. The implant of claim 1, wherein the projection includes respective proximal and distal ends that are opposite one another along the first direction, and includes a ramped surface that extends from the respective proximal end of the projection to the respective distal end of the projection.

11. An implant configured to be implanted into an intervertebral space between first and second vertebrae, the implant comprising:
  a first component having proximal and distal ends that are spaced from one another along a first direction, a first pair of sides that are spaced from one another along a second direction, perpendicular to the first direction, and a first inner surface and a first outer surface that are spaced from one another along a third direction, perpendicular to both the first and second directions, the first outer surface configured to grip one of the first and second vertebrae, the first component defining a through hole that extends through the first inner and first outer surfaces, and the first component further defining a recess that extends into the first inner surface with respect to the third direction and terminates between the first inner surface and first outer surface; and a second component having proximal and distal ends that are spaced from one another along the first direction, a second pair of sides that are spaced from one another along the second direction, and a second inner surface and a second outer surface that are spaced from one another along the third direction, the second inner surface facing the first inner surface, and the second outer surface configured to grip another one of the first and second vertebrae, the second component defining a through hole that extends through the second inner surface and the second outer surface, wherein the implant further comprises a projection that has a maximum length along the second direction that is greater a maximum width and maximum height of the projection along the first direction and third directions, respectively, and the projection being configured to be received by the recess, the projection including a ramped surface that defines an incline with respect to the first and second inner surfaces as the projection extends along the first direction.

12. The implant of claim 11, wherein the first and second inner surfaces extend parallel to an insertion direction of the implant that is oriented along the first direction.

13. The implant of claim 11, wherein the through hole of the second component is aligned with the through hole of the first component.

14. The implant of claim 11, wherein the recess extends at least partially into the each side of the first pair of sides along the second direction.

15. The implant of claim 11, wherein the projection includes respective proximal and distal ends that are opposite one another along the first direction, and the ramped surface extends from the respective proximal end of the projection to the respective distal end of the projection.

16. The implant of claim 11, wherein the ramped surface extends in a direction that is towards the first outer surface of the first component as the ramped surface extends along an insertion direction of the implant that is oriented along the first direction.

17. The implant of claim 11, wherein the projection limits movement of the first component along the first direction.

18. The implant of claim 11, wherein the distal end of the first component is tapered.

19. The implant of claim 11, wherein the recess is defined by first and second internal surfaces that are opposite one another along the first direction.

20. An implant configured to be implanted into an intervertebral space between first and second vertebrae, the implant comprising:

a first component having proximal and distal ends that are spaced from one another along a first direction, a first pair of sides that are spaced from one another along a second direction, perpendicular to the first direction, and a first inner surface and a first outer surface that are spaced from one another along a third direction, perpendicular to both the first and second directions, the first outer surface configured to grip one of the first and second vertebrae, the first component defining a through hole that extends through the first inner and first outer surfaces, and the first component further defining a recess that extends into the first inner surface with respect to the third direction and terminates between the first inner surface and first outer surface; and a second component having proximal and distal ends that are spaced from one another along the first direction, a second pair of sides that are spaced from one another along the second direction, and a second inner surface and a second outer surface that are spaced from one another along the third direction, the second inner surface facing the first inner surface, and the second outer surface configured to grip another one of the first and second vertebrae, the second component defining a through hole that extends through the second inner surface and the second outer surface, wherein the implant further comprises a projection that is elongate along the second direction and configured to be received by the recess, the projection including a ramped surface that defines an incline with respect to the first and second inner surfaces as the projection extends along the first direction, and the projection including respective proximal and distal ends that are opposite one another along the first direction, the ramped surface extending from the respective proximal end of the projection to the respective distal end of the projection.

21. The implant of claim 20, wherein the first and second inner surfaces extend parallel to an insertion direction of the implant that is oriented along the first direction.

22. The implant of claim 20, wherein the recess extends at least partially into the each side of the first pair of sides along the second direction.

23. The implant of claim 20, wherein the ramped surface extends in a direction that is towards the first outer surface of the first component as the ramped surface extends along an insertion direction of the implant that is oriented along the first direction.

* * * * *